United States Patent
Yudovsky

(10) Patent No.: US 9,619,883 B2
(45) Date of Patent: Apr. 11, 2017

(54) SYSTEMS AND METHODS FOR EVALUATING HYPERSPECTRAL IMAGING DATA USING A TWO LAYER MEDIA MODEL OF HUMAN TISSUE

(71) Applicant: Hypermed Imaging, Inc., Memphis, TN (US)

(72) Inventor: Dmitry Yudovsky, Los Angeles, CA (US)

(73) Assignee: Hypermed Imaging, Inc., Memphis, TN (US)

(*) Notice: Subject to any disclaimer, the term of this patent is extended or adjusted under 35 U.S.C. 154(b) by 17 days.

(21) Appl. No.: 14/776,681

(22) PCT Filed: Mar. 17, 2014

(86) PCT No.: PCT/US2014/030930
§ 371 (c)(1),
(2) Date: Sep. 14, 2015

(87) PCT Pub. No.: WO2014/146053
PCT Pub. Date: Sep. 18, 2014

(65) Prior Publication Data
US 2016/0042513 A1 Feb. 11, 2016

Related U.S. Application Data

(60) Provisional application No. 61/802,170, filed on Mar. 15, 2013.

(51) Int. Cl.
*G06K 9/00* (2006.01)
*G06T 7/00* (2017.01)
(Continued)

(52) U.S. Cl.
CPC .......... *G06T 7/0016* (2013.01); *G06F 19/321* (2013.01); *G06T 7/003* (2013.01);
(Continued)

(58) Field of Classification Search
CPC .............. G06F 19/00; G06K 9/00; G06T 7/00
(Continued)

(56) References Cited

U.S. PATENT DOCUMENTS 7,865,231 B2 * 1/2011 Tearney .............. A61B 1/00165
600/407
8,224,425 B2 * 7/2012 Freeman .............. A61B 5/0059
600/473

\* cited by examiner

*Primary Examiner* — Abolfazl Tabatabai
(74) *Attorney, Agent, or Firm* — Brett A. Lovejoy; Andrew J. Antczak; Morgan, Lewis & Bockius, LLP

(57) ABSTRACT

The disclosure provides computer systems, non-transitory computer-readable storage medium, and methods for determining the presence of a skin indication in a subject. In some aspects the method includes acquiring a hyperspectral imaging data set from a region of interest of a human subject using a hyperspectral imager, and applying the hyperspectral imaging data set against a classifier including a two layered media model, the two layered media model including a first layer of a modeled human tissue overlying a second layer of the modeled human tissue, where the two layered media model has been trained by application of simulated data across a set of optical and geometric properties associated with the presence or the absence of a skin indication, where the two layered media model computes tissue reflectance R from the modeled human tissue by a relationship provided herein.

37 Claims, 19 Drawing Sheets

(51) Int. Cl.
*G06F 19/00* (2011.01)
*A61B 5/05* (2006.01)
(52) U.S. Cl.
CPC ............... *G06T 2207/10004* (2013.01); *G06T 2207/20081* (2013.01); *G06T 2207/30088* (2013.01)
(58) Field of Classification Search
USPC ....... 382/128, 129, 130, 131, 132, 133, 134; 378/18; 600/410, 313, 334, 338, 442, 562
See application file for complete search history.

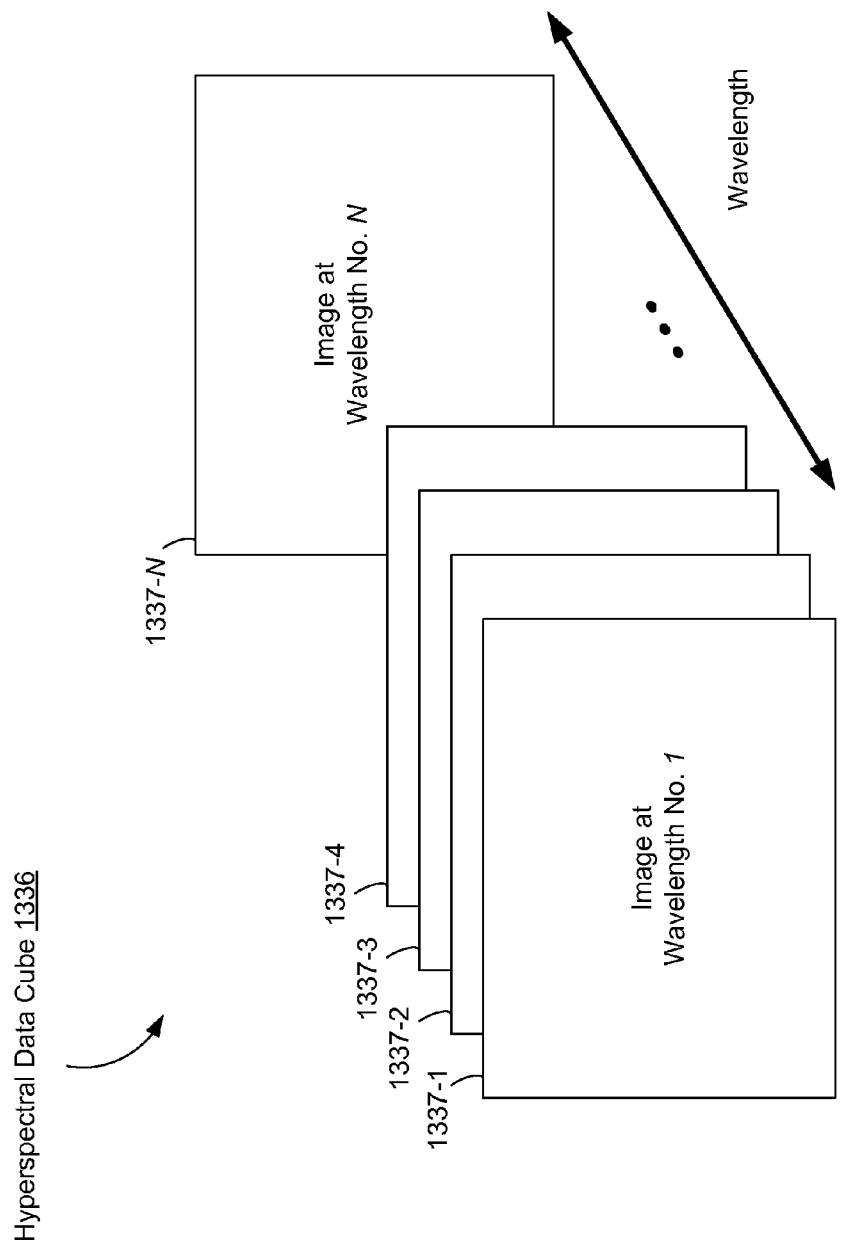

Acquire a hyperspectral imaging data set from a region of interest of a human subject using a hyperspectral imager ⎯1730

Apply the hyperspectral imaging data against a classifier including a two layered media model, the two layered media model including a first layer of a modeled human tissue overlying a second layer of the modeled human tissue, where the two layered media model was trained by application of simulated data from a set of photons across a set of optical and geometric properties associated with the presence or the absence of a skin indication, where the two layered media model computes tissue reflectance R from the modeled human tissue by the relationship: ⎯1740

$$R = \frac{W_{total}}{P} = W_0 \sum_{i=0}^{\infty} \sum_{j=0}^{\infty} (\omega_1)^i (\omega_2)^j P(i,j|L_1)$$

where, $W_{total}$ is the total energy remitted by the set of photons, $P$ is the number of photons in the set of photons, $W_0$ is the initial energy of each photon in the set of photons, $\omega_1$ is the single scattering albedo of the first layer, $\omega_2$ is the single scattering albedo of the second layer, $L_1$ is the thickness of the first layer, and $P(i,j|L_1)$ is a joint probability density function that a respective photon in the set of photons will experience $i$ interactions with the first layer and $j$ interactions with the second layer given the first layer thickness $L_1$, and where the application of the hyperspectral imaging data set against the classifier causes the classifier to produce a determination as to whether the region of interest has the skin indication

Figure 7B

1750 — Acquire a hyperspectral imaging data set from a region of interest of a human subject using a hyperspectral imager 1760 — Apply the hyperspectral imaging data set against a classifier including a two layered media model, the two layered media model including a first layer of a modeled human tissue overlying a second layer of the modeled human tissue, where the two layered media model was trained by application of simulated data from a set of photons across a set of optical and geometric properties associated with the presence or the absence of a skin indication, where the two layered media model computes tissue reflectance $R$ from the modeled human tissue by the relationship:

$$R = \alpha_0 \sum_{i=0}^{\infty} \sum_{j=0}^{\infty} \exp(i\tilde{\omega}_1 + j\tilde{\omega}_2) P(i,j|\tilde{L}_1)$$

where, $\alpha_0$ is a constant for losses arising from surface reflectance or the acceptance angle of the hyperspectral imager, exp is the exponential function, $i$ is an integer, $j$ is an integer, $\tilde{\omega}_1 = \log\omega_1$, $\tilde{\omega}_2 = \log\omega_2$, $\omega_1$ is the single scattering albedo of the first layer, $\omega_2$ is the single scattering albedo of the second layer, $\tilde{L}_1 = L_1\mu_{t,1}$, $\mu_{t,1}$ is the total interaction coefficient of the first layer, $L_1$ is the thickness of the top layer, and $P(i,j|L_1)$ is a joint probability density function that a photon in the set of photons will experience $i$ interactions with the first layer and $j$ interactions with the second layer given $\tilde{L}_1$

Figure 7C

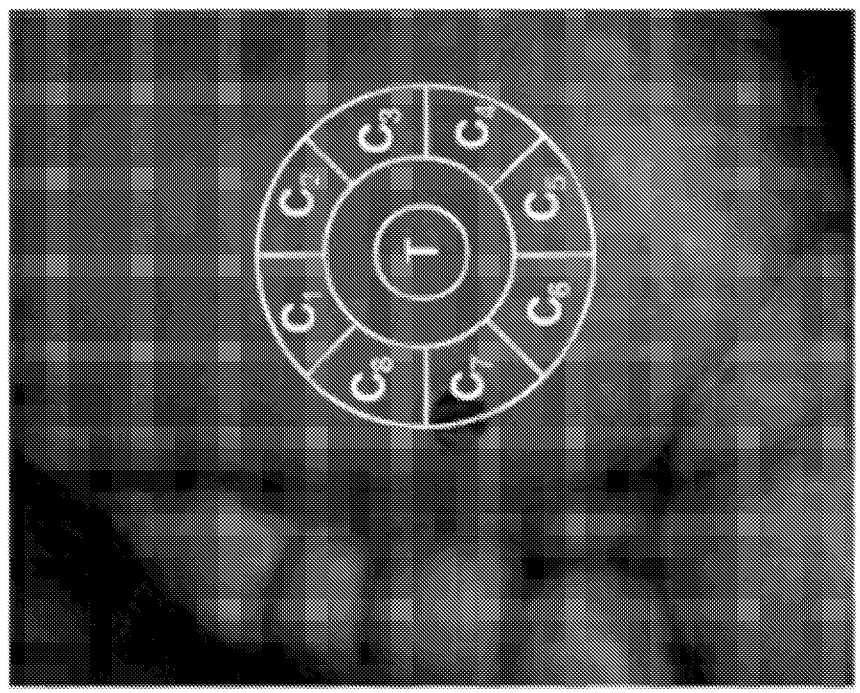
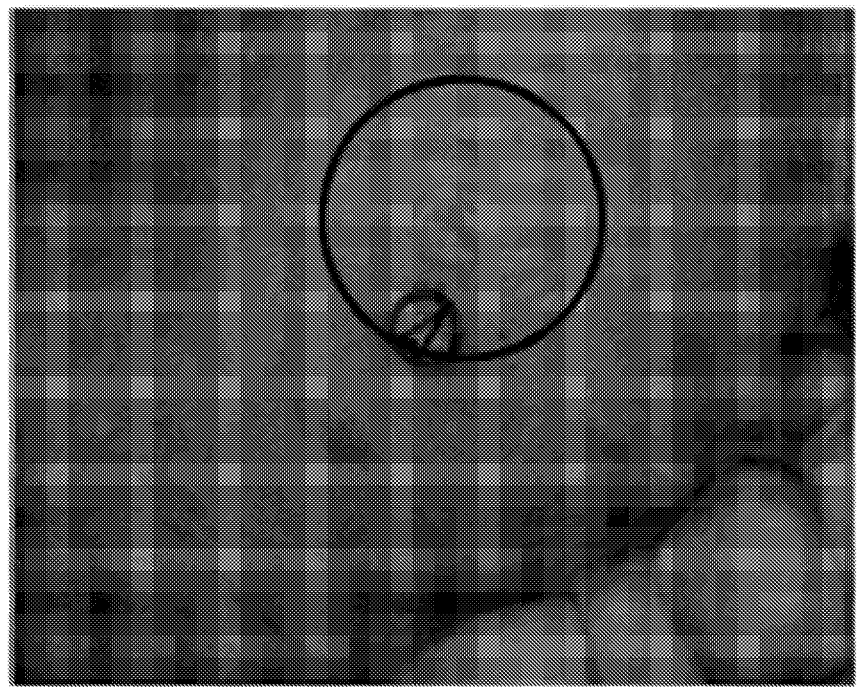
Figure 8

SYSTEMS AND METHODS FOR EVALUATING HYPERSPECTRAL IMAGING DATA USING A TWO LAYER MEDIA MODEL OF HUMAN TISSUE

CROSS REFERENCE TO RELATED APPLICATION

This application claims priority to U.S. Patent Application No. 61/802,170, filed Mar. 15, 2013, which is hereby incorporated by reference herein in its entirety.

TECHNICAL FIELD

The present disclosure relates to hardware and software for automated and accurate detection of healthy versus ulcerating tissue on the diabetic foot using visible and near infrared (NIR) wavelengths.

BACKGROUND

Hyperspectral (also known as "multispectral") spectroscopy is an imaging technique that integrates multiples images of an object resolved at different spectral bands (i.e., ranges of wavelengths) into a single data structure, referred to as a three-dimensional hyperspectral data cube. Hyperspectral spectroscopy is often used to identify an individual component of a complex composition through the recognition of corresponding spectral signatures of the individual components in a particular hyperspectral data cube.

Hyperspectral spectroscopy has been used in a variety of applications, ranging from geological and agricultural surveying to military surveillance and industrial evaluation. Hyperspectral spectroscopy has also been used in medical applications to facilitate complex diagnosis and predict treatment outcomes. For example, medical hyperspectral imaging has been used to accurately predict viability and survival of tissue deprived of adequate perfusion, and to differentiate diseased (e.g. tumor) and ischemic tissue from normal tissue.

Some known oximetry algorithms that make use of Hyperspectral data operate by (i) irradiating the human tissue with narrow bands of light in the visible range, (ii) acquiring co-registered images of the tissue under the above illumination, (iii) calculating a reflectance signal from the tissue by normalizing the tissue reflectance signal by the reflectance from a highly reflective calibration standard, (iv) calculating the apparent absorption of tissue by taking the logarithm of the measured normalized reflectance signal, (v) calculating contribution of the absorption coefficient spectra of oxy-hemoglobin and deoxy-hemoglobin to the absorption spectrum of skin, and (vi) creating a map of weights for oxy- and deoxy-hemoglobin.

Such methods apply the so-called modified Beer-Lambert's (the MBL) law to analyze the reflectance image. The primary assumptions and limitations of this approach further include the limitation that tissue is modeled as homogeneous with depth. Then, nothing can be said about callus formation since this is primarily a change in the structure of the epidermis, the top layer of skin. A further limitation is that the tissue scattering coefficient is constant with wavelength. This assumption introduces little error for small wavelength ranges (e.g., the visible range). However, the accuracy of MBL diminishes if applied to a much larger range, say visible through near infrared.

Despite its limitations, such known oximetry techniques exhibit clinically relevant ulcer formation prediction capabilities. A description of such an algorithm is provided in Yudovsky and Durkin, 2011, "Spatial Frequency Domain Spectroscopy of Two Layer Media," Journal of Biomedical Optics 16, 107005, (hereinafter "JBO-002") which is hereby incorporated by reference herein in its entirety. In short, ulcer development prediction algorithms have been developed. They have been used to collect hyperspectral image data from the feet of multiple diabetic subjects exhibiting diabetic ulceration and at risk of forming new diabetic ulcers.

Over the course of one such study, a group of subjects with ulcers were observed to heal. A second group with ulcers was observed not to heal. Yet a third group was observed to develop new ulcers. Data from the first and second groups were used to develop an ulcer healing index described in Nouvong et al., "Evaluation of Diabetic Foot Ulcer Healing With Hyperspectral Imaging of Oxyhemoglobin and Deoxyhemoglobin," Diabetes Care 32, 2056 (hereinafter "DC-001") which is hereby incorporated by reference herein in its entirety. Data from the third group were used to develop the Formation Prediction Algorithm described in Yudovsky, 2011, "Assessing diabetic foot ulcer development risk with hyperspectral tissue oximetry," Journal of Biomedical Optics 16, 026009 (hereinafter "JBO-001"), which is hereby incorporated by reference herein in its entirety.

The Formation Prediction Algorithm was calibrated by retrospectively analyzing the OXY and DEOXY signals as depicted in FIG. 8. Locations of formed ulcers were retrospectively analyzed for large changes in OXY/DEOXY signals. An area indicated by "T" was centered on the site known to become an ulcer. The average OXY and DEOXY values were calculated in that area. The same procedure was performed in all eight control regions ($C_1$ through $C_8$ in FIG. 8(b) around the test region. Then, the maximum difference was found between T and $C_i$ for both OXY and DEOXY signals. The resulting maximum differences (MDs) are plotted for 21 subjects in FIG. 9 along with results from the same analysis performed at the contralateral site and 100 random locations on the feet of the diabetic subjects. Then, a threshold was drawn to separate ulcerating points in the first and third quadrants from other points. Then, any HSI image can be analyzed and points that fall within the "Affected tissue" areas highlighted in as indicated in FIG. 10.

Careful analysis of FIGS. 9 and 10 shows a significant number of false positive predictions. In fact, JBO-001 reported a sensitivity and specificity of 95% and 80%, respectively. The implications of these numbers are (i) 5% of affected tissue may not be detected and (ii) 20% of tissue identified as unaffected may in fact be healthy.

An attempt to improve these numbers of was made by developing a two layered model of human tissue as summarized in Yudowsky, 2010, "Two-Layer Optical Model of Skin for Early, Non-Invasive Detection of Wound Development on the Diabetic Foot," Advanced Biomedical and Clinical Diagnostic Systems VIII, edited by Tuan Vo-Dinh, Warren S. Grundfest, Anita Mahadevan-Jansen, Proc. of SPIE Vol. 7555, 755514, 2010 SPIE (hereinafter "SPIE-001"), which in turn references Yudovsky, 2009, "Simple and accurate expressions for diffuse reflectance of semi-infinite and two-layer absorbing and scattering media," Applied Optics 48, No. 35 (hereinafter "AO-001") and Yudowsky, 2009, "Rapid and accurate estimation of blood saturation, melanin content, and epidermis thickness from spectral diffuse reflectance," Applied Optics 49, 1707 (hereinafter "AO-002"), each of which is hereby incorporated by reference herein in its entirety. In short, a two layer model of light transfer through skin in the visible range (500 to 650 nm) was developed. The model calculated tissue reflectance as a function of melanin concentration, epidermal thickness, blood volume, saturation, and tissue scattering. AO-002 describes the application of the model developed in AO-001 to reflectance from human tissue. See also Yudovsky et al. 2011, "Assessing diabetic foot ulcer development risk with hyperspectral tissue oximetry," Journal of Biomedical Optics 16, 026009-1 (hereinafter "JBP-001"), which is hereby incorporated by reference in its entirety.

Furthermore, Yudovsky et al., 2011, "Monitoring temporal development and healing of diabetic foot ulceration using hyperspectral imaging," J. Biophotonics 4, No. 7-8, 565-576 (hereinafter "JBP-002"), which is hereby incorporated herein by reference in its entirety, shows the application of the model and method described in SPIE-001 to the temporal monitoring of ulcer development and healing. References 14 and 15 of JBP-002 explain that callus formation (epidermal thickening) are caused by excessive sheer pressure on the diabetic foot. Furthermore, callus formation exacerbates the pressure as the callus grows and thus leads to ulceration. FIGS. 4 and 5 of JBP-002 shows the average epidermal thickness on a preulcerative area on the feet of two diabetic subjects before, during, and after ulceration. FIG. 11 (adopted from FIG. 8 of JPB-002) shows epidermal thickness at an ulcer site and a control site before ulceration and during healing for one subject. It was observed that the epidermal thickness was larger on the affected area when compared with a control area on the other foot. Furthermore, the thickness increased from a baseline of 130 µm to 170 µm at the point of ulceration. Then, the skin thickness near the ulcer site decreased as the ulcer healed to near baseline.

JBP-002 showed the applicability of the model and method described in SPIE-001 to monitoring the temporal development of ulcers by detecting the formation of the thickening callus cap that forms above an ulcer. Furthermore, it showed that thinning of the callus around the ulcer as the ulcer heals. The development and use of the model described in AO-001 and AO-002 constitute an improvement over known algorithms that only provide oximetry information. Many more parameters can be detected from tissue reflectance in the visible range. The analysis described in JBP-002 establishes the possibility that HSI—with proper modeling—can be used to not only predict ulcer formation but also provide an estimate on the speed of ulcer formation by measuring the growth and receding of the callus cap.

Some known tissue oximetry algorithms are based on a homogeneous MBL law model of light transfer through skin in the visible range (500 to 650 nm). The explicit limitations of such models and choice of interrogation wavelength include that they are limited to detection of oxy and deoxy hemoglobin in the superficial tissue of skin. Visible light does not penetrate more than 1 millimeter. Further, such know methods cannot detect melanin concentration because pigmentation is treated as nuisance parameters and calibrated away. Further still, they cannot be extended to beyond the visible range because (i) it is calibrated for visible light and (ii) it is derived with the assumption of static scattering coefficient. This implies that detection of water content (hydration) is not feasible with such algorithms without major modification. Further still, such algorithms cannot be extended to detect epidermal thickness since this requires an explicit treatment of light transfer through the two layers of skin. Also, they are typically calibrated specifically to human tissue on the arms and feet. It is thus difficult to apply the same technology to other external and internal organs. Moreover, callus completely occludes the dermal signal in the visible range thus making oximetry over thick calluses unsatisfactory in the visible range. In such approaches, ulcer prediction is based on the OXY and DEOXY values and so the determination of healthy/non-healthy tissue in FIG. 9 is determined by a linear classifier with two parameters. Further, the output of such known algorithms, as exemplified in FIG. 10, shows Boolean classification. In fact, a tissue area may have a likelihood of ulceration, with some areas more likely to ulcerate than others. Further still, the output of such algorithms, as exemplified in FIG. 10, do not give a sense of time to ulceration. Presented with FIG. 10, a clinician has no sense of likelihood of ulcer formation one, two three, etc. weeks after imaging.

The model presented in SPIE-001 and applications presented in JBP-002 represent improvements in the field. However, the model presented in SPIE-001 has limitations. For instance, the model accurately predicts light transfer in the visible range (500 to 600 nm). The accuracy of the model diminishes below the useful threshold beyond 600 nm since human skin becomes highly scattering (see FIGS. 9 and 10 in AO-001). Further, the two layer model presented in AO-001 exhibits an error in predicting reflectance from two layer media of up to 8%. Additionally, the error in predicting the reflectance depends on the range of input optical and geometric values. A sensor with offset/noise that is proportional to the measured quantity is undesirable in medical applications where accuracy is essential. The careful reviewer will see that the model presented in AO-001 and AO-002 shows feasibility but does not constitute a production solution. The inverse method presented in AO-002 is based on the forward model presented in AO-001. Measured reflectance is compared to output from the modeled reflectance and then the input parameters to the model are iteratively modified until the modeled and measured reflectance are identical within a tolerable error. The iteration typically converges after 100 attempts. An HSI may contain on the order of 100,000 pixels. Thus, calculation speed is important.

The model presented in AO-001 is computationally intense. For example, the images in JBP-002 took many hours to produce on a desktop. An industrial implementation of JBP-002 would likely require highly paralyzed embedded devices such as a DSP or GPU. Such devices are efficient at processing simple functions with few steps. Thus, the AO-001 model would be cumbersome to implement on a single digital signal processor or graphic processor unit because it is complex and requires multiple look up tables. It is thus difficult to productize.

There are limitations of the results presented in JBP-002 with regard to temporal analysis of callus formation and receding. Callus on the healthy or diabetic foot can be millimeters thick. However, epidermal thickness presented in JBP-002 ranges between 0 and 150 µm (+150 µm tests the accuracy of the model presented in AO-001). It is likely that the epidermal thickness presented in JBP-002 is sensitive to true epidermal thickness but may not have a linear relationship to the physical quantity. The range of wavelengths used by typical oximetry algorithms that are limited to visible light spectrums may also affect the estimation of epidermal thickness. Epidermal tissue is highly absorbing in the visible range. Thus an epidermis of 150 µm and 1500 µm will have essentially the same reflectance in the visible range since light does not penetrate the callus to the deeper layers. In both cases, the callus will look like a semi-infinite (one layer) and no useful information about the dermis and the true epidermal thickness can be determined. NIR light can penetrate a thick callus. The combination of visible and NIR reflectance provides a complete view of the tissue. The visible light primarily interrogates the epidermis while the NIR light primarily interrogates the dermis. It is like looking at a wall and then looking through the wall at the content behind. A complete picture of the entire building can be reported. Clinically, temporal data from only two patients was analyzed. This is not enough to develop a predictive index that also gives a time-to-ulceration or speed of ulceration score.

Given the above background, what is needed in the art are improvement methods for performing tissue oximetry.

SUMMARY

Various implementations of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various implementations are used to enable improved ulcer formation detection.

In a first aspect, the disclosure provides a computer implemented method, performed by a computer system having one or more processors and memory storing one or more programs for execution by the one or more processors, the method including: acquiring a hyperspectral imaging data set from a region of interest of a human subject using a hyperspectral imager, and applying the hyperspectral imaging data set against a classifier comprising a two layered media model, the two layered media model comprising a first layer of a modeled human tissue overlying a second layer of the modeled human tissue. This two layered media model has been trained by application of simulated data across a set of optical and geometric properties associated with the presence or the absence of a skin indication, where the two layered media model computes tissue reflectance R from the modeled human tissue by the relationship:

$$R = \sum_{i=0}^{\infty} \sum_{j=0}^{\infty} \exp(i\tilde{\omega}_1 + j\tilde{\omega}_2) P(i, j | L_1)$$

where, $L_1$ is the thickness of the first layer, $\tilde{\omega}_1$ is a modified single scattering of the first layer, $\tilde{\omega}_2$ is a modified single scattering of the second layer, exp is the exponential function, and $P(i,j|L_1)$ is a joint probability density function that a photon will experience i interactions with the first layer and j interactions with the second layer given that the first layer thickness is $L_1$. The application of the hyperspectral imaging data set against the classifier causes the classifier to produce a determination as to whether the region of interest has the skin indication.

In some embodiments, the classifier is an artificial neural network. In some embodiments, the classifier is linear regression, non-linear regression, logistic regression, multivariate data analysis, classification using a regression tree, partial least squares projection to latent variables, computation of a neural network, computation of a Bayesian model, computation of a generalized additive model, use of a support vector machine, or modeling comprising boosting or adaptive boosting. See, for example, Duda et al., 2001, *Pattern Classification*, Second Edition, John Wiley & Sons, Inc., New York; Hastie, 2003, *The Elements of Statistical Learning*, Springer, New York; and Agresti 1996, *An Introduction to Categorical Data Analysis*, John Wiley & Sons, New York, each of which is hereby incorporated by reference herein for such purpose.

In one embodiment of the first aspect described above, the determination as to whether the region of interest has the skin indication is a likelihood that the region of interest has the skin indication.

In one embodiment of the first aspect described above, the determination as to whether the region of interest has the skin indication is either a determination that the region of interest has the skin indication or a determination that the region of interest does not have the skin indication.

In one embodiment of the first aspect described above, the method further includes training the model using the trajectory vector $\vec{x}_p$ of each respective photon p in a set of photons comprising a million or more photons.

In one embodiment of the first aspect described above, the trajectory vector $\vec{x}_p$ of each respective photon p in the set of photons is computed using a scaled or white Monte Carlo simulation.

In one embodiment of the first aspect described above, where, for each respective photon in the set of photons, the trajectory vector $\vec{x}_p$ of the respective photon was calculated such that $\vec{x}_{p,k} = \langle x, y, z \rangle_k$ represents the location of the $k^{th}$ interaction between the photon and the two layer model and wherein the trajectory vector $\vec{x}_p$ was stored in a non-transitory data file.

In one embodiment of the first aspect described above, $P(i,j|L_1)$ is approximated as $$\frac{N(i, j | L_1)}{P},$$

where $N(i,j|L_1)$ is a count of the set of photons in the set of photons that experience i interactions with the first layer and j interactions with the second layer given $L_1$, and has the form:

$$N(i, j | L_1) = \sum_{p=1}^{p=P} \begin{cases} 1 & N_{p,1} = i \text{ and } N_{p,2} = j \\ 0 & \text{otherwise} \end{cases}$$

where, $N_{p,1}$ is a number of interactions between photon p and the first layer, $N_{p,2}$ is a number of interactions between photon p and the second layer, and P is the number of photons in the set of photons.

In one embodiment of the first aspect described above, the hyperspectral imaging data set includes a plurality of images of the region of interest, each respective image in the plurality of images acquired at a wavelength in one or more of the ultra-violet (UV), visible, near infra-red (NIR), and infra-red (IR) spectral regions.

In one embodiment of the first aspect described above, the hyperspectral imaging data set includes a plurality of images of the region of interest, each respective image in the plurality of images acquired at a wavelength in the visible or NIR spectral regions.

In one embodiment of the first aspect described above, at least one respective image in the plurality of images is acquired at a wavelength in the visible spectral region and at least one respective image in the plurality of images is acquired at a wavelength in the NIR spectral region.

In one embodiment of the first aspect described above, the hyperspectral imaging data set includes a plurality of images acquired without contacting the human subject.

In one embodiment of the first aspect described above, the hyperspectral imaging data set includes a plurality of images acquired endoscopically, laparoscopically, thoracoscopically, cystoscopically, hysteroscopically, bronchoscopically, or mediastinoscopically.

In one embodiment of the first aspect described above, the hyperspectral imaging data set includes a plurality of images of the region of interest, the method further comprising: prior to applying the hyperspectral imaging data set against the classifier, pre-processing at least one image in the plurality of images by performing at least one of: adjusting the brightness of the image, adjusting the contrast of the image, removing an artifact from the image, cropping the image, processing one or more sub-pixels of the image, compressing the size of the image, assembling a plurality of images into a spectral hypercube, transforming a spectral hypercube assembled from the plurality of images, formatting data contained within the image, and encrypting data contained within the image.

In one embodiment of the first aspect described above, the hyperspectral imaging data set is transmitted to a remote computer system by wireless communication.

In one embodiment of the first aspect described above, the remote computer system is a mobile device, and the transmission is by wired or wireless communication.

In one embodiment of the first aspect described above, the mobile device is selected from the group consisting of a smart phone, a personal digital assistant (PDA), an enterprise digital assistant, a tablet computer, a digital camera, and a portable music player.

In one embodiment of the first aspect described above, the skin indication is selected from the group consisting of tissue ischemia, an ulcer, peripheral artery disease, atherosclerosis, chronic venous insufficiency, lower extremity deep venous thrombosis, infection, shock, hypovolemia, diabetes, dehydration, hemorrhage, hemorrhagic shock, hypertension, cancer, a retinal abnormality, a skin wound, a burn wound, exposure to a chemical or biological agent, and an inflammatory response.

In one embodiment of the first aspect described above, the skin indication is a diabetic foot ulcer.

In one embodiment of the first aspect described above, the skin indication is a pressure ulcer.

In one embodiment of the first aspect described above, the skin indication is a cancerous skin legion.

In one embodiment of the first aspect described above, the skin indication is a cancerous tumor.

In one embodiment of the first aspect described above, the skin indication is a particular stage of a cancer.

In a second aspect, the disclosure provides a computer system, including one or more processors, memory, and one or more programs, the one or more programs stored in the memory and configured to be executed by the one or more processors, the one or more programs including instructions for: acquiring a hyperspectral imaging data set from a region of interest of a human subject collected by a hyperspectral imager, and applying the hyperspectral imaging data set against a classifier comprising a two layered media model, the two layered media model comprising a first layer of a modeled human tissue overlying a second layer of the modeled human tissue. The two layered media model has been trained by application of simulated data across a set of optical and geometric properties associated with the presence or the absence of a skin indication, wherein the two layered media model computes tissue reflectance R from the modeled human tissue by the relationship:

$$R = \sum_{i=0}^{\infty} \sum_{j=0}^{\infty} \exp(i\tilde{\omega}_1 + j\tilde{\omega}_2) P(i, j \mid L_1)$$

where, $L_1$ is the thickness of the first layer, $\tilde{\omega}_1$ is a modified single scattering of the first layer, $\tilde{\omega}_2$ is a modified single scattering of the second layer, exp is the exponential function, and $P(i,j|L_1)$ is a joint probability density function that a photon will experience i interactions with the first layer and j interactions with the second layer given that the first layer thickness is $L_1$. The application of the hyperspectral imaging data set against the classifier causes the classifier to produce a determination as to whether the region of interest has the skin indication.

In a third aspect, the disclosure provides a computer implemented method, performed by a computer system having one or more processors and memory storing one or more programs for execution by the one or more processors, the method comprising: acquiring a hyperspectral imaging data set from a region of interest of a human subject using a hyperspectral imager, and applying the hyperspectral imaging data set against a classifier comprising a two layered media model, the two layered media model comprising a first layer of a modeled human tissue overlying a second layer of the modeled human tissue, wherein the two layered media model has been trained by application of simulated data from a set of photons across a set of optical and geometric properties associated with the presence or the absence of a skin indication, wherein the two layered media model computes tissue reflectance R from the modeled human tissue by the relationship:

$$R = \frac{W_{total}}{P} = w_0 \sum_{i=0}^{\infty} \sum_{j=0}^{\infty} (\omega_1)^i (\omega_2)^j P(i, j \mid L_1)$$

where, $W_{total}$ is the total energy remitted by the set of photons, P is the number of photons in the set of photons, $W_0$ is the initial energy of each photon in the set of photons, $\omega_1$ is the single scattering albedo of the first layer, $\omega_2$ is the single scattering albedo of the second layer, $L_1$ is the thickness of the first layer, $P(i,j|L_1)$ is a joint probability density function that a respective photon in the set of photons will experience i interactions with the first layer and j interactions with the second layer given the first layer thickness $L_1$. The application of the hyperspectral imaging data set against the classifier causes the classifier to produce a determination as to whether the region of interest has the skin indication.

In one embodiment of the third aspect described above, the two layer model requires $\mu_{a,1} + \mu_{s,1} = \mu_{a,2} + \mu_{s,2} = 1 \text{ cm}^{-1}$, where, $\mu_{a,1}$ is the absorption interaction coefficient for the first layer, $\mu_{s,1}$ is the scattering interaction coefficient for the first layer, $\mu_{a,2}$ is the absorption interaction coefficient for the second layer, and $\mu_{s,2}$ is the scattering interaction coefficient for the second layer.

In one embodiment of the third aspect described above, the determination as to whether the region of interest has the skin indication is a likelihood that the region of interest has the skin indication.

In one embodiment of the third aspect described above, the determination as to whether the region of interest has the skin indication is either a determination that the region of interest has the skin indication or a determination that the region of interest does not have the skin indication.

In one embodiment of the third aspect described above, the set of photons comprises a million or more photons.

In one embodiment of the third aspect described above, $P(i,j|L_1)$ is approximated as $$\frac{N(i, j | L_1)}{P},$$

where $N(i,j|L_1)$ is a count of the number of photons in the set of photons that experience i interactions with the first layer and j interactions with the second layer given $L_1$, and has the form:

$$N(i, j | L_1) = \sum_{p=1}^{p=P} \begin{cases} 1 & N_{p,1} = i \text{ and } N_{p,2} = j \\ 0 & \text{otherwise} \end{cases}$$

where, $N_{p,1}$ is a number of interactions between respective photon p and the first layer, $N_{p,2}$ is a number of interactions between respective photon p and the second layer, and P is the number of photons in the set of photons.

In one embodiment of the third aspect described above, the two layer model allows $\mu_{a,1}+\mu_{s,1} \neq 1$, where, $\mu_{a,1}$ is the absorption interaction coefficient for the first layer, and $\mu_{s,1}$ is the scattering interaction coefficient for the first layer.

In one embodiment of the third aspect described above, $P(i,j|L_1)=P(i,j|\tilde{L}_1)=P(i,j|\tilde{L}_1,\tilde{\mu}_{a,1},\tilde{\mu}_{s,1})$, where, $$\frac{\mu_{a,1}}{\mu_{t,1}} \to \tilde{\mu}_{a,1}, \frac{\mu_{s,1}}{\mu_{t,1}} \to \tilde{\mu}_{s,1}, \mu_{t,1} = \mu_{a,1} + \mu_{s,1}, L_1\mu_{t,1} \to \tilde{L}_1,$$

and "$\to$" indicates equivalence under $P(i,j|L_1)$.

In one embodiment of the third aspect described above, the two layer model allows $\mu_{a,2}+\mu_{s,2} \#1$, where, $\mu_{a,2}$ is the absorption interaction coefficient for the second layer, and $\mu_{s,2}$ is the scattering interaction coefficient for the second layer.

In one embodiment of the third aspect described above, $P(i,j|L_1)=P(i,j|\tilde{L}_1)=P(i,j|\tilde{L}_1,\tilde{\mu}_{a,1},\tilde{\mu}_{s,1},\mu_{t,2}=1,\omega_2)$, where, $\mu_{a,1}$ is the absorption interaction coefficient for the first layer, and $\mu_{s,1}$ is the scattering interaction coefficient for the first layer, $$\mu_{t,1} = \mu_{a,1} + \mu_{s,1}, \frac{\mu_{a,1}}{\mu_{t,1}} \to \tilde{\mu}_{a,1}, \frac{\mu_{s,1}}{\mu_{t,1}} \to \tilde{\mu}_{s,1}, L_1\mu_{t,1} \to \tilde{L}_1,$$

and "$\to$" indicates equivalence under $P(i,j|L_1)$.

In one embodiment of the third aspect described above, the hyperspectral imaging data set includes a plurality of images of the region of interest, each image in the plurality of images acquired at a wavelength in one or more of the ultra-violet (UV), visible, near infra-red (NIR), and infra-red (IR) spectral regions.

In one embodiment of the third aspect described above, the hyperspectral imaging data set includes a plurality of images of the region of interest, each image in the plurality of images acquired at a wavelength in the visible or NIR spectral regions.

In one embodiment of the third aspect described above, at least one respective image in the plurality of images is acquired at a wavelength in the visible spectral region and at least one respective image in the plurality of images is acquired at a wavelength in the NIR spectral region.

In one embodiment of the third aspect described above, the hyperspectral imaging data set includes a plurality of images acquired without contacting the human subject.

In one embodiment of the third aspect described above, the hyperspectral imaging data set includes a plurality of images acquired endoscopically, laparoscopically, thoracoscopically, cystoscopically, hysteroscopically, bronchoscopically, or mediastinoscopically.

In one embodiment of the third aspect described above, the hyperspectral imaging data set includes a plurality of images of the region of interest, the method further including: prior to applying the hyperspectral imaging data set against the classifier, pre-processing at least one image in the plurality of images by performing at least one of: adjusting the brightness of the image, adjusting the contrast of the image, removing an artifact from the image, cropping the image, processing one or more sub-pixels of the image, compressing the size of the image, assembling a plurality of images into a spectral hypercube, transforming a spectral hypercube assembled from the plurality of images, formatting data contained within the image, and encrypting data contained within the image.

In one embodiment of the third aspect described above, the hyperspectral imaging data set is transmitted to a remote computer system by wireless communication.

In one embodiment of the third aspect described above, the remote computer system is a mobile device.

In one embodiment of the third aspect described above, the mobile device is selected from the group consisting of a smart phone, a personal digital assistant (PDA), an enterprise digital assistant, a tablet computer, a digital camera, and a portable music player.

In one embodiment of the third aspect described above, the skin indication is selected from the group consisting of tissue ischemia, an ulcer, peripheral artery disease, atherosclerosis, chronic venous insufficiency, lower extremity deep venous thrombosis, infection, shock, hypovolemia, diabetes, dehydration, hemorrhage, hemorrhagic shock, hypertension, cancer, a retinal abnormality, a skin wound, a burn wound, exposure to a chemical or biological agent, and an inflammatory response.

In one embodiment of the third aspect described above, the skin indication is a diabetic foot ulcer.

In one embodiment of the third aspect described above, the skin indication is a pressure ulcer.

In one embodiment of the third aspect described above, the skin indication is a cancerous skin legion.

In one embodiment of the third aspect described above, the skin indication is a cancerous tumor.

In one embodiment of the third aspect described above, the skin indication is a particular stage of a cancer.

In a fourth aspect, the disclosure provides a computer system, including one or more processors, memory, and one or more programs, the one or more programs stored in the memory and configured to be executed by the one or more processors, the one or more programs including instructions for: acquiring a hyperspectral imaging data set from a region of interest of a human subject collected by a hyperspectral imager, and applying the hyperspectral imaging data set against a classifier comprising a two layered media model, the two layered media model comprising a first layer of a modeled human tissue overlying a second layer of the modeled human tissue, wherein the two layered media model has been trained by application of simulated data from a set of photons across a set of optical and geometric properties associated with the presence or the absence of a skin indication, wherein the two layered media model computes tissue reflectance R from the modeled human tissue by the relationship:

$$R = \frac{W_{total}}{P} = w_0 \sum_{i=0}^{\infty} \sum_{j=0}^{\infty} (\omega_1)^i (\omega_2)^j P(i, j | L_1)$$

wherein, $W_{total}$ is the total energy remitted by the set of photons, P is the number of photons in the set of photons, $W_0$ is the initial energy of each photon in the set of photons, $\omega_1$ is the single scattering albedo of the first layer, $\omega_2$ is the single scattering albedo of the second layer, $L_1$ is the thickness of the first layer, $P(i,j|L_1)$ is a joint probability density function that a respective photon in the set of photons will experience i interactions with the first layer and j interactions with the second layer given the first layer thickness $L_1$. The application of the hyperspectral imaging data set against the classifier causes the classifier to produce a determination as to whether the region of interest has the skin indication.

In a fifth aspect, the disclosure provides a computer implemented method, performed by a computer system having one or more processors and memory storing one or more programs for execution by the one or more processors, the method including: acquiring a hyperspectral imaging data set from a region of interest of a human subject using a hyperspectral imager, and applying the hyperspectral imaging data set against a classifier comprising a two layered media model, the two layered media model comprising a first layer of a modeled human tissue overlying a second layer of the modeled human tissue, wherein the two layered media model has been trained by application of simulated data from a set of photons across a set of optical and geometric properties associated with the presence or the absence of a skin indication, wherein the two layered media model computes tissue reflectance R from the modeled human tissue by the relationship:

$$R = \alpha_0 \sum_{i=0}^{\infty} \sum_{j=0}^{\infty} \exp(i\tilde{\omega}_1 + j\tilde{\omega}_2) P(i, j | \tilde{L}_1)$$

where, $\alpha_0$ is a constant for losses arising from surface reflectance or the acceptance angle of the hyperspectral imager, exp is the exponential function, i is an integer, j is an integer, $\tilde{\omega}_1 = \log \omega_1$, $\tilde{\omega}_2 = \log \omega_2$, $\omega_1$ is the single scattering albedo of the first layer, $\omega_2$ is the single scattering albedo of the second layer, $\tilde{L}_1 = L_1 \mu_{t,1}$, $\mu_{t,1}$ is the total interaction coefficient of the first layer, $L_1$ is the thickness of the top layer, and $P(i,j|L_1)$ is a joint probability density function that a photon in the set of photons will experience i interactions with the first layer and j interactions with the second layer given $\tilde{L}_1$.

In one embodiment of the fifth aspect described above, the determination as to whether the region of interest has the skin indication is a likelihood that the region of interest has the skin indication.

In one embodiment of the fifth aspect described above, the determination as to whether the region of interest has the skin indication is either a determination that the region of interest has the skin indication or a determination that the region of interest does not have the skin indication.

In one embodiment of the fifth aspect described above, the set of photons comprises a million or more photons.

In one embodiment of the fifth aspect described above, the hyperspectral imaging data set includes a plurality of images of the region of interest, each image in the plurality of images acquired at a wavelength in one or more of the ultra-violet (UV), visible, near infra-red (NIR), and infra-red (IR) spectral regions.

In one embodiment of the fifth aspect described above, the hyperspectral imaging data set includes a plurality of images of the region of interest, each image in the plurality of images acquired at a wavelength in the visible or NIR spectral regions.

In one embodiment of the fifth aspect described above, at least one respective image in the plurality of images is acquired at a wavelength in the visible spectral region and at least one respective image in the plurality of images is acquired at a wavelength in the NIR spectral region.

In one embodiment of the fifth aspect described above, the hyperspectral imaging data set includes a plurality of images acquired without contacting the human subject.

In one embodiment of the fifth aspect described above, the hyperspectral imaging data set includes a plurality of images acquired endoscopically, laparoscopically, thoracoscopically, cystoscopically, hysteroscopically, bronchoscopically, or mediastinoscopically.

In one embodiment of the fifth aspect described above, the hyperspectral imaging data set includes a plurality of images of the region of interest, the method further including: prior to applying the hyperspectral imaging data set against the classifier, pre-processing at least one image in the plurality of images by performing at least one of: adjusting the brightness of the image, adjusting the contrast of the image, removing an artifact from the image, cropping the image, processing one or more sub-pixels of the image, compressing the size of the image, assembling a plurality of images into a spectral hypercube, transforming a spectral hypercube assembled from the plurality of images, formatting data contained within the image, and encrypting data contained within the image.

In one embodiment of the fifth aspect described above, the hyperspectral imaging data set is transmitted to a remote computer system by wireless communication.

In one embodiment of the fifth aspect described above, the remote computer system is a mobile device.

In one embodiment of the fifth aspect described above, the mobile device is selected from the group consisting of a smart phone, a personal digital assistant (PDA), an enterprise digital assistant, a tablet computer, a digital camera, and a portable music player.

In one embodiment of the fifth aspect described above, the skin indication is selected from the group consisting of tissue ischemia, an ulcer, peripheral artery disease, atherosclerosis, chronic venous insufficiency, lower extremity deep venous thrombosis, infection, shock, hypovolemia, diabetes, dehydration, hemorrhage, hemorrhagic shock, hypertension, cancer, a retinal abnormality, a skin wound, a burn wound, exposure to a chemical or biological agent, and an inflammatory response.

In one embodiment of the fifth aspect described above, the skin indication is a diabetic foot ulcer.

In one embodiment of the fifth aspect described above, the skin indication is a pressure ulcer.

In one embodiment of the fifth aspect described above, the skin indication is a cancerous skin legion.

In one embodiment of the fifth aspect described above, the skin indication is a cancerous tumor.

In one embodiment of the fifth aspect described above, the skin indication is a particular stage of a cancer.

In a sixth aspect, the disclosure provides a computer system, including one or more processors, memory, and one or more programs, the one or more programs stored in the memory and configured to be executed by the one or more processors, the one or more programs including instructions for: acquiring a hyperspectral imaging data set from a region of interest of a human subject collected by a hyperspectral imager, and applying the hyperspectral imaging data set against a classifier comprising a two layered media model, the two layered media model comprising a first layer of a modeled human tissue overlying a second layer of the modeled human tissue, wherein the two layered media model has been trained by application of simulated data from a set of photons across a set of optical and geometric properties associated with the presence or the absence of a skin indication, wherein the two layered media model computes tissue reflectance R from the modeled human tissue by the relationship:

$$R = \alpha_0 \sum_{i=0}^{\infty} \sum_{j=0}^{\infty} \exp(i\tilde{\omega}_1 + j\tilde{\omega}_2) P(i, j \mid \tilde{L}_1)$$

where, $\alpha_0$ is a constant for losses arising from surface reflectance or the acceptance angle of the hyperspectral imager, exp is the exponential function, i is an integer, j is an integer, $\tilde{\omega}_1 = \log \omega_1$, $\tilde{\omega}_2 = \log \omega_2$, $\omega_1$ is the single scattering albedo of the first layer, $\omega_2$ is the single scattering albedo of the second layer, $\tilde{L}_1 = L_1 \mu_{t,1}$, $\mu_{t,1}$ is the total interaction coefficient of the first layer, $L_1$ is the thickness of the top layer, and $P(i,j|L_1)$ is a joint probability density function that a photon in the set of photons will experience i interactions with the first layer and j interactions with the second layer given $\tilde{L}_1$.

In one embodiment of the methods described above, the set of optical and geometric properties comprises tissue oxygen saturation $SO_2$, total hemoglobin concentration $f_{HEME}$, melanin concentration $f_{mel}$, tissue water concentration $f_{H_2O}$, epidermal thickness $L_1$ and wavelength range.

In one embodiment of the methods described above, the training was performed with $SO_2$ between 0% and 100%, $f_{HEME}$ between 0 and 200 μM, $f_{mel}$ between 0.002 μM and 0.15 μM, $f_{H_2O}$ between 0 and 100%, and $L_1$ between 10 μm and 150 μm.

In one embodiment of the methods described above, the training was performed at each of between 5 and 20 wavelengths.

In one embodiment of the methods described above, the first layer is a melanin pigmented epidermis and the second layer is a blood pigmented dermis.

In one embodiment of the computer systems described above, the set of optical and geometric properties comprises tissue oxygen saturation $SO_2$, total hemoglobin concentration $f_{HEME}$, melanin concentration $f_{mel}$, tissue water concentration $f_{H_2O}$, epidermal thickness $L_1$ and wavelength range.

In one embodiment of the computer systems described above, wherein the training was performed with $SO_2$ between 0% and 100%, $f_{HEME}$ between 0 and 200 μM, $f_{mel}$ between 0.002 μM and 0.15 μM, $f_{H_2O}$ between 0 and 100%, and $L_1$ between 10 μm and 150 μm.

In one embodiment of the computer systems described above, the training was performed at each of between 5 and 20 wavelengths.

In one embodiment of the computer systems described above, the first layer is a melanin pigmented epidermis and the second layer is a blood pigmented dermis.

In one embodiment of the computer systems described above, the first layer is a melanin pigmented epidermis and the second layer is a blood pigmented dermis.

In one embodiment of the methods described above, the skin indication is an ulcer, the method further includes detecting at least one physiological change selected from: inflammation of the ulcer and surrounding areas, necrosis, callus formation around the ulcer site, loss of the epidermal layer, and hyper-pigmentation.

BRIEF DESCRIPTION OF THE DRAWINGS

So that the present disclosure can be understood in greater detail, a more particular description may be had by reference to aspects of various implementations, some of which are illustrated in the appended drawings. The appended drawings, however, merely illustrate the more pertinent aspects of the present disclosure and are therefore not to be considered limiting, as the description may admit to other effective aspects and arrangements.

FIG. 6 is a schematic illustration of a hyperspectral data cube.

FIG. 7B is a flowchart representation of an implementation of a method of applying a hyperspectral imaging data set against a classifier comprising a two layered media model in accordance with a second aspect of the present disclosure.

FIG. 7C is a flowchart representation of an implementation of a method of applying a hyperspectral imaging data set against a classifier comprising a two layered media model in accordance with a third aspect of the present disclosure.

FIGS. 8A and 8B respectively illustrates (i) an image of a plantar ulcer (circles) developed on an affected diabetic subject and (ii) an image of the same foot without ulceration 116 days earlier, with target and adjacent regions centered on the location of the affected are not drawn to scale.

Figure 1:
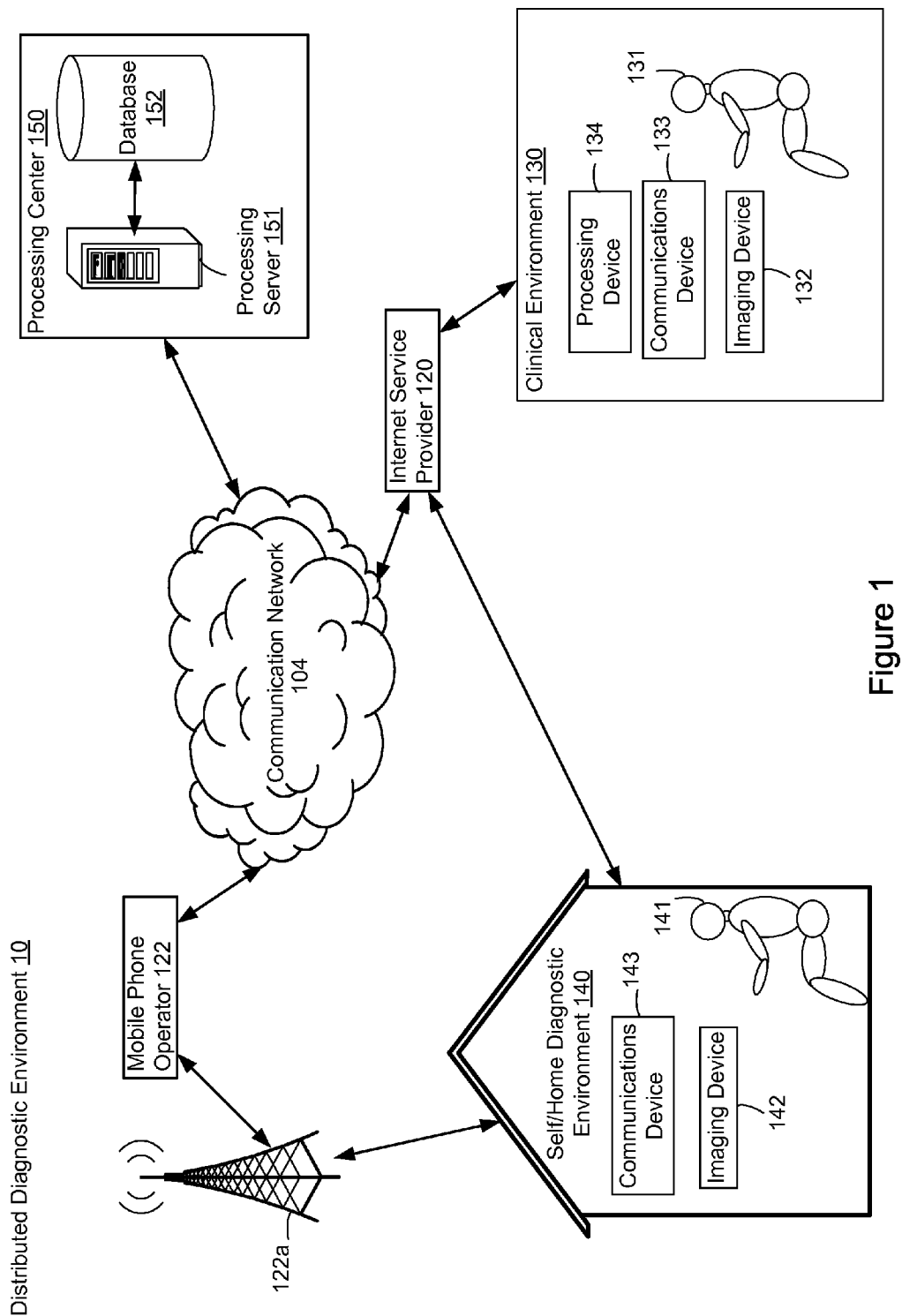
FIG. 1 is an example of a distributed diagnostic environment including single-sensor hyperspectral imaging devices according to some implementations.

In accordance with common practice the various features illustrated in the drawings may not be drawn to scale. The dimensions of various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Numerous details are described herein in order to provide a thorough understanding of the example implementations illustrated in the accompanying drawings. However, the invention may be practiced without many of the specific details. Well-known methods, components, and circuits have not been described in exhaustive detail so as not to unnecessarily obscure more pertinent aspects of the implementations described herein.

First reference is made with respect to FIGS. 1 through 6 of exemplary hyperspectral imager environments that can be used to implement the methods of the present disclosure. FIG. 7 then provides an example of a flow chart in accordance with an aspect of the present disclosure.

FIG. 1 is an example of a distributed diagnostic environment 10 including a single-sensor hyperspectral imaging device 132/142 according to some implementations. In some implementations, the distributed diagnostic environment 10 includes one or more clinical environments 130, one or more self/home diagnostic environments 140, one or more processing centers 150, and a communication network 104 that, together with one or more Internet Service Providers 120 and/or Mobile phone operators 122, with concomitant cell towers 122a, allow communication between the one or more environments 130/140 and the one or more processing centers 150.

Turning to the self/home diagnostic environment 140 depicted in FIG. 1, an advantage of the present disclosure is that the hyperspectral imager is small and portable, allowing for the realization of the disclosed environment 140. The self/home diagnostic environment 140 includes an imaging device 142 and a communications device 143. The communications device 143 communicates with processing center 150 via communications network 140.

In some implementations, the imaging device 142 illuminates an object (e.g., an area of the body of a subject 141) and generates imaging data of the object. In some implementations, the imaging device 142 illuminates an object using one or more light sources (not shown). In some implementations, after illuminating the object, or concurrently thereto, the imaging device 142 generates and transmits imaging data (e.g., the hyperspectral image data set) corresponding to the object to processing center 150 for forming a processed hyperspectral image. In other implementations, the imaging device 142 forms the processed hyperspectral image using the hyperspectral image data set, and transmits the processed hyperspectral image to the processing center 150.

The clinical environment 130 depicted in FIG. 1 is similar to the self/home diagnostic environment 140. The exception is that the clinical environment 130 is designed to test several patients 131. To accommodate this demand, in some embodiments, the clinical environment 130 includes a processing device 134 for processing hyperspectral images without reliance on processing center 150. As such, in some embodiments, the clinical environment 130 includes the processing device 134, a communications device 133, and an imaging device 132. The communications device 133 communicates with processing center 150 via communications network 140.

In some implementations, the imaging device 132 illuminates an object (e.g., an area of the body of a patient 131) and generates imaging data of the object. In some implementations, the imaging device 132 illuminates an object using one or more light sources (not shown). In some implementations, after illuminating the object, or concurrently thereto, the imaging device 132 generates and transmits imaging data (e.g., the hyperspectral image data set) corresponding to the object to processing center 150 for forming a processed hyperspectral image. In other implementations, the imaging device 132 transmits the hyperspectral image data set to processing device 134 where the processed hyperspectral image is formed using the hyperspectral image data. In some embodiments, processing device 134 is a desktop computer, a laptop computer, and/or a tablet computer. In still other implementations, the imaging device 132 forms the processed hyperspectral image using the hyperspectral image data set, and transmits the processed hyperspectral image to the processing center 150 via communications device 133.

In some implementations, prior to transmitting the hyperspectral imaging data set, the imaging device 132 transforms the imaging data by performing at least one of adjusting the brightness of at least one of the respective digital images in the hyperspectral imaging data, adjusting the contrast of at least one of the respective digital images in the hyperspectral imaging data, removing an artifact from at least one of the respective digital images in the hyperspectral imaging data, cropping at least one of the respective digital images in the hyperspectral imaging data, processing one or more sub-pixels of at least one of the respective digital images in the hyperspectral imaging data, compressing the size of at least one of the respective digital images in the hyperspectral imaging data, assembling a plurality of digital images in the hyperspectral imaging data into a hyperspectral data cube, transforming a hyperspectral data cube, formatting data contained within at least one of the respective digital images in the hyperspectral imaging data, and encrypting data contained within at least one of the respective digital images in the hyperspectral imaging data.

The processing center 150 depicted in FIG. 1 receives images from self/home diagnostic environment and/or clinical environment 130 and processes them using processing server 151 before storing them using database 152 for subsequent retrieval.

Figure 2:
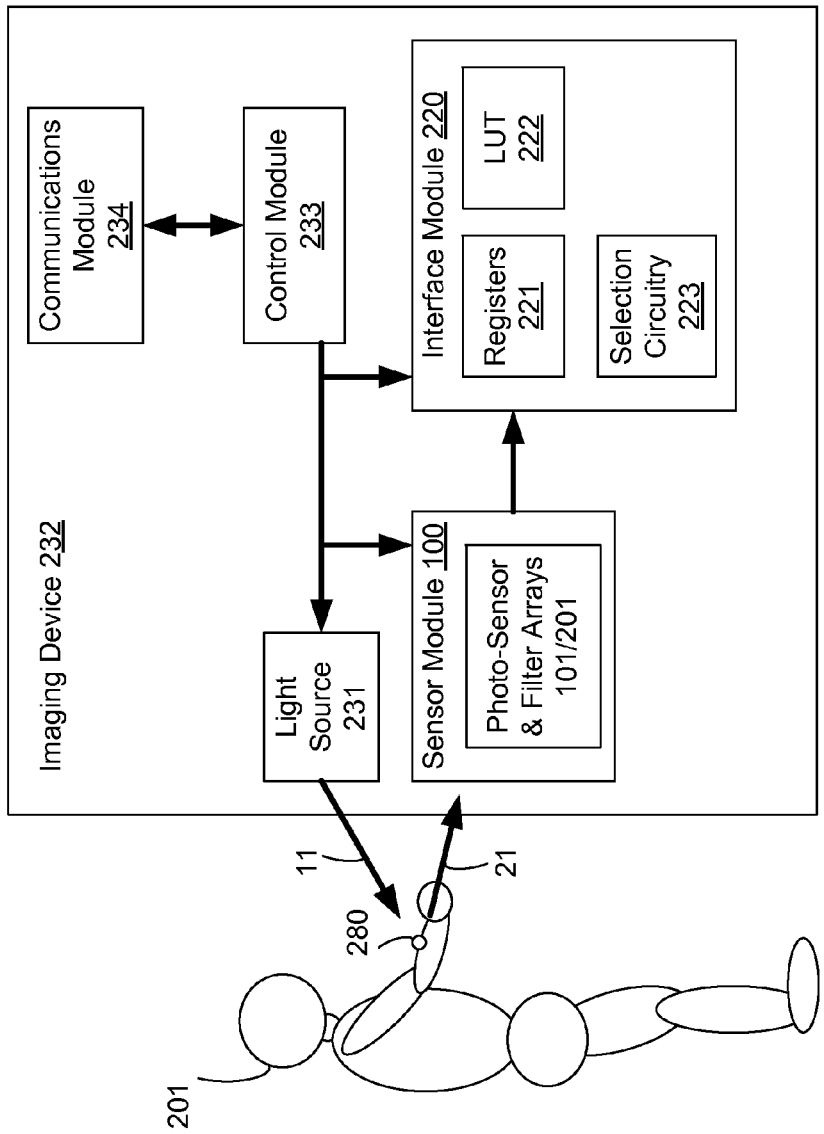
FIG. 2 is a schematic diagram of a local diagnostic environment according to some embodiments of the present disclosure.

FIG. 2 is a schematic diagram of a local diagnostic environment 200 according to some implementations. Local diagnostic environment 200 differs from distributed diagnostic environment in the sense that there is no requirement that the local diagnostic environment make use of a processing center 150 for the storage and/or processing of hyperspectral images. The local diagnostic environment 200 includes an imaging device 232 and a communications module 234. The communications module 234 is used, for example, to optionally communicate hyperspectral imaging data to a remote location and/or to receive software updates or diagnostic information.

In some implementations, the imaging device 232 illuminates an object (e.g., an area 280 of the body of a subject 201) and generates imaging data of the object. In some implementations, the imaging device 232 illuminates an object using one or more light sources (231). Such light sources emit light 11 that is reflected by area 280 to form reflected light 21 that is received by sensor module 100. Sensor module 100 includes photo-sensor and filter arrays 101/201.

In some embodiments, output of the photo-sensor and filter arrays 101/201 is sent to registers 221 of an interface module 220 and processed by one or more register look-up tables 222 and selection circuitry 223. For instance, in some embodiments, look-up table 222 is used in the following manner. In such embodiments, for purposes of illustration, registers 221 is a plurality of registers. The hyperspectral imaging device 232 uses the registers 221 to receive the output of the photo-sensor array 101 and the control module 223 identifies which registers 221 in the plurality of registers correspond to filter elements of a particular filter-type in a plurality of filter-types using the look-up table. The control module 223 selects one or more subsets of photo-sensor outputs from the plurality of registers based on the identification of the registers that correspond to filter elements of the particular filter-type. The independent subsets of photo-sensors are then used to form independent images, each image corresponding to a filter-type.

Operation of the light source 231, sensor module 100 and interface module 220 is under the control of control module 233. In some embodiments, as illustrated in FIG. 2, control module 233, in turn, interacts with a communications module 234 in order to facilitate the acquisition of hyperspectral imaging data from a subject 201.

In various embodiments, light sources emitting radiation in the ultraviolet spectrum (wavelengths from about 10 nm to about 400 nm), visible spectrum (wavelengths from about 400 nm to about 760 nm), and/or near-infrared spectrum (wavelengths from about 760 nm to about 2000 nm) are used in the hyperspectral/multispectral imaging systems and methods provided herein.

In some implementations, light source 231 includes one or more broadband light sources, one or more narrowband light source, or a combination of one or more broadband light source and one or more narrowband light source. In some implementations, light source 231 includes one or more coherent light sources, one or more incoherent light sources, or a combination of one or more coherent and one or more incoherent light sources.

In some implementations, light source 231 includes one or more narrow bandwidth LED lights. In one implementation, the one or more narrowband LED lights have a FWHM spectral bandwidth or less than about 100 nm, preferably less than about 50 nm, more preferably less than 25 nm. In one implementation, light source 231 includes one or more LED source that emits radiation in the infrared, preferably near-infrared, spectrum. The used of near-infrared LED illumination in is commonly found in closed circuit security cameras. For additional information on light emitting diodes, see, Schubert E. F., *Light Emitting Diodes*, Second Edition, Cambridge University Press (2006), the content of which is hereby incorporated herein by reference in its entirety for all purposes.

Figure 3:
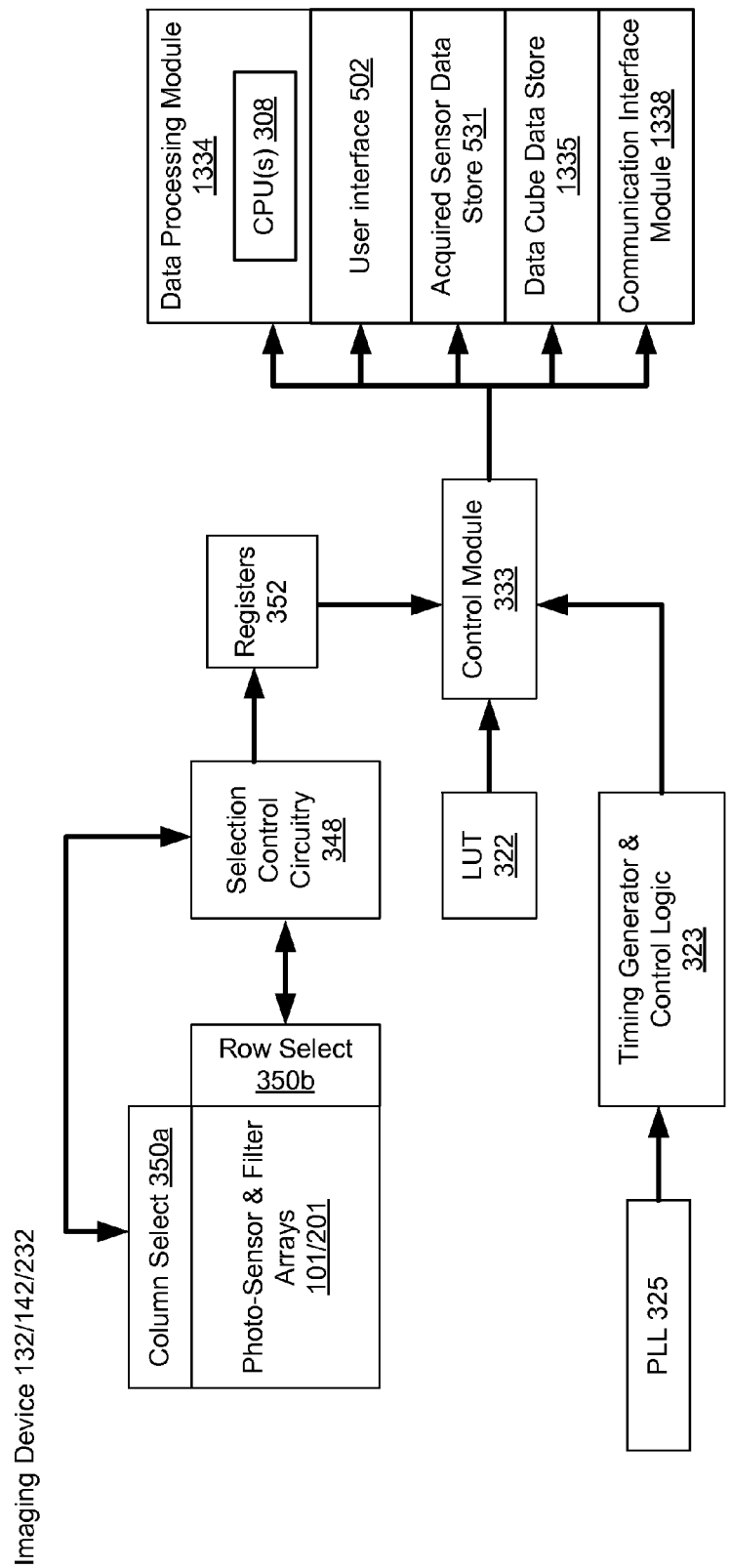
FIG. 3 is a detailed diagram of an example implementation of a single-sensor hyperspectral imaging device in accordance with some embodiments of the present disclosure.

FIG. 3 is a detailed diagram of an example implementation of a single-sensor hyperspectral imaging device 132/142/232 in accordance with the present disclosure. In general, the timing generator and control logic 323 controls frame exposure mode timing, frame rate adjustment, and frame rate timing. In some embodiments, timing generator and control logic 323 relies on phased-lock loop 325 (PLL) for timing signals. These aforementioned components work in conjunction with a control module 333 and look-up table 322 to control acquisition of images from the photo-sensor and filter arrays 101/102. To this end, there is selection control circuitry 348 to select data using column select 350a and row select 350b circuitry. This data is stored and processed in registers 352. This data is passed, under the direction of the control module 333 to data processing module 1334 which works in conjunction with user interface 502, acquired sensor data store 531, data cube data store 1335, and communication interface module 1338. These modules, interfaces and data stores are described in more detail below on conjunction with FIG. 5.

Figure 4:
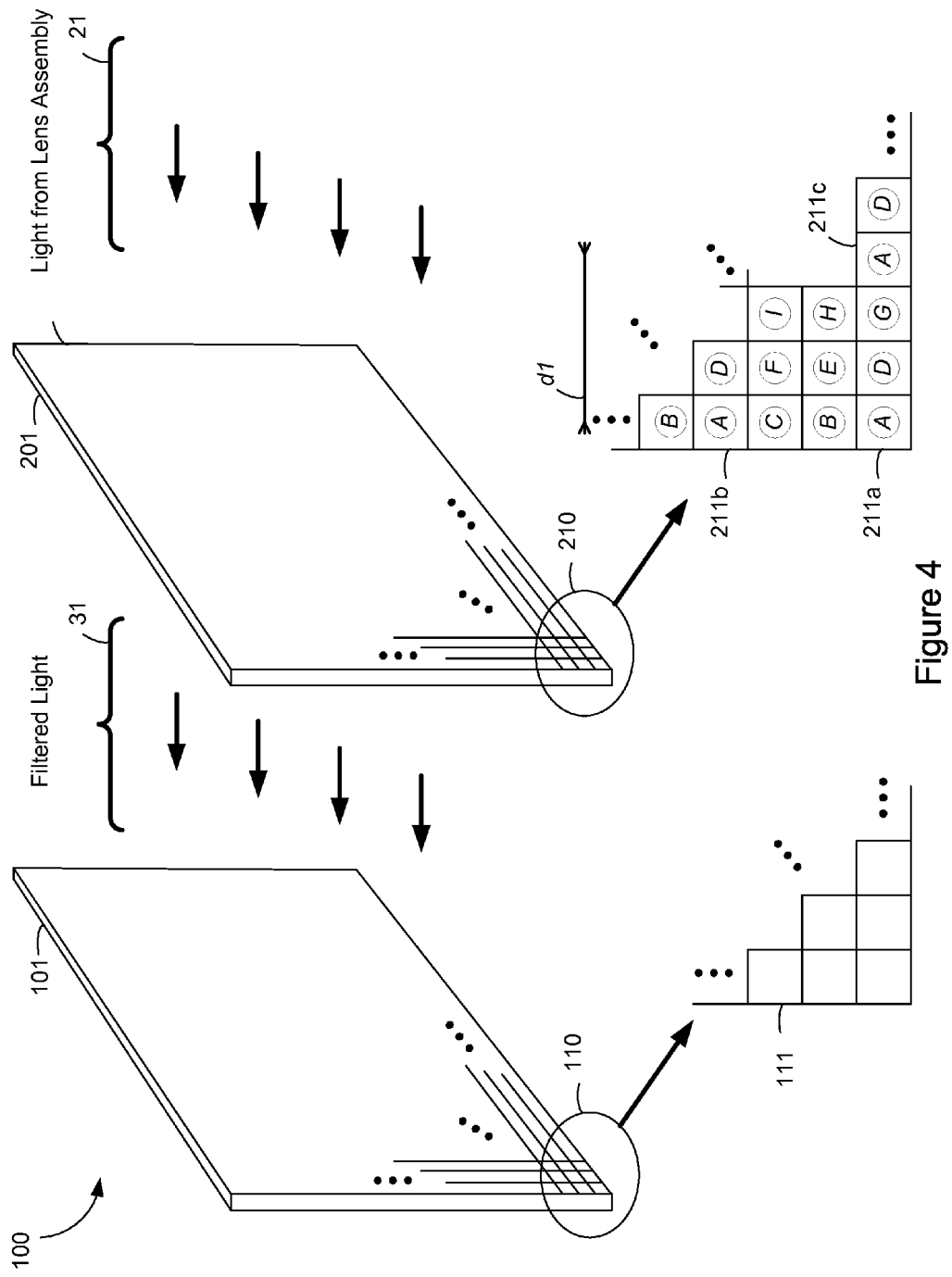
FIG. 4 is an exploded schematic view of an implementation of an image sensor assembly in accordance with some embodiments of the present disclosure.

FIG. 4 is an exploded schematic view of an implementation of an exemplary image sensor assembly for a single-sensor hyperspectral imaging device 132/142/232. The image sensor assembly 100 includes a photo-sensory array 101 in combination with a filter array 201. While some example features are illustrated in FIG. 4, those skilled in the art will appreciate from the present disclosure that various other features have not been illustrated for the sake of brevity and so as not to obscure more pertinent aspects of the example implementations disclosed herein. For example, the various electrical connections and access control circuitry to receive the outputs of the photo-sensor array 101 have not been illustrated. Nevertheless, those skilled in the art will appreciate that at least one of various configurations of electrical connections and access control circuitry to receive the outputs of the photo-sensor array 101 would be included in an operable single-sensor hyperspectral imaging device. Moreover, an interface module and a controller—which are together configured to select, assemble, process, and analyze the outputs of the photo-sensor array 101 into a hyperspectral data cube—are described above with reference to FIG. 3.

With further reference to FIG. 4, in some implementations, the photo-sensory array 101 includes a plurality of photo-sensors. For example, detailed view 110 schematically shows, as a non-limiting example only, a number of photo-sensors 111 included in the photo-sensor array 101. Each photo-sensor 111 generates a respective electrical output by converting light incident on the photo-sensor.

In some implementations, the photo-sensor array 101 includes a CCD (charge coupled device) semiconductor sensor array. A CCD sensor is typically an analog device. When light strikes a CCD sensor array, the light is converted to and stored as an electrical charge by each photo-sensor. The charges are converted to voltage, on a photo-sensor by photo-sensor basis, as they are read from the CCD sensor array. Often, but not exclusively, one photo-sensor is synonymous with a respective single pixel. However, in various implementations, a single pixel is configured to include two or more pixels.

In some implementations, the photo-sensor array 101 includes a CMOS (complementary metal oxide) semiconductor sensor array. A CMOS photo-sensor is an active photo-sensor that includes a photodetector and an active amplifier. In other words, each photo-sensor in a CMOS sensor array includes a respective photodetector and a corresponding active amplifier.

In some implementations, the photo-sensor array 101 includes a hybrid CCD/CMOS sensor array. In some implementations, a hybrid CCD/CMOS sensor array includes CMOS readout integrated circuits (ROICs) that are bump bonded to a CCD imaging substrate. In some implementations, a hybrid CCD/CMOS sensor array is produced by utilizing the fine dimensions available in modern CMOS technology to implement a CCD like structure in CMOS technology. This can be achieved by separating individual poly-silicon gates by a very small gap.

The light incident on a particular photo-sensor 111 is filtered by a respective filter in the filter array 201. In some implementations, the filter array 201 is configured to include a plurality of filter elements. Each filter element is arranged to filter light received by a respective one or more of the plurality of photo-sensors in the photo-sensor array 101. Each filter element is also one of a plurality of filter-types, and each filter-type is characterized by a spectral pass-band different from the other filter-types. As such, the electrical output of a particular photo-sensor is associated with a particular spectral pass-band associated with the respective filter associated the particular photo-sensor 111.

For example, the detailed view 210 schematically shows, as a non-limiting example only, a number of filter-types A, B, C, D, E, F, G, H, and I are included in the filter array 201. In one implementation, at least two of filter types A, B, C, D, E, F, G, H, and I have different spectral pass-bands. For example, as illustrated in FIG. 4, filter elements 211a-1 and 211a-2 of filter types A and B, respectively, have different spectral pass-bands. In some implementations, at least two of filter types A, B, C, D, E, F, G, H, and I have the same spectral pass-band and at least two of filter types A, B, C, D, E, F, G, H, and I have different spectral pass-bands.

In some implementations, each filter-type A, B, C, D, E, F, G, H, and I has a spectral pass-band different from the others. In some implementations, the filter-types A, B, C, D, E, F, G, H, and I are arranged in a 3×3 grid that is repeated across the filter array 201. For example, as illustrated in FIG. 4, three filter elements 211a-1, 211b-1, 211c-1 of filter-type A are illustrated to show that instances of filter-type A are repeated in a uniform distribution across the filter array 201 such that the center-to-center distance d1 between two filters of the same type is less than 250 microns in some implementations. In some implementations, the center-to-center distance d1 between two filters of the same type is less than 100 microns.

Moreover, while nine filter-types are illustrated for example in FIG. 4, those skilled in the art will appreciate from the present disclosure that any number of filter types can be used in various implementations. For example, in some implementations 3, 5, 16 or 25 filter-types can be used in various implementations. Additionally and/or alternatively, while a uniform distribution of filter-types has been illustrated and described, those skilled in the art will appreciate from the present disclosure that, in various implementations, one or more filter-types may be distributed across a filter array in a non-uniform distribution. Additionally and/or alternatively, those skilled in the art will also appreciate that "white-light" or transparent filter elements may be included as one of the filter-types in a filter array.

Figure 5:
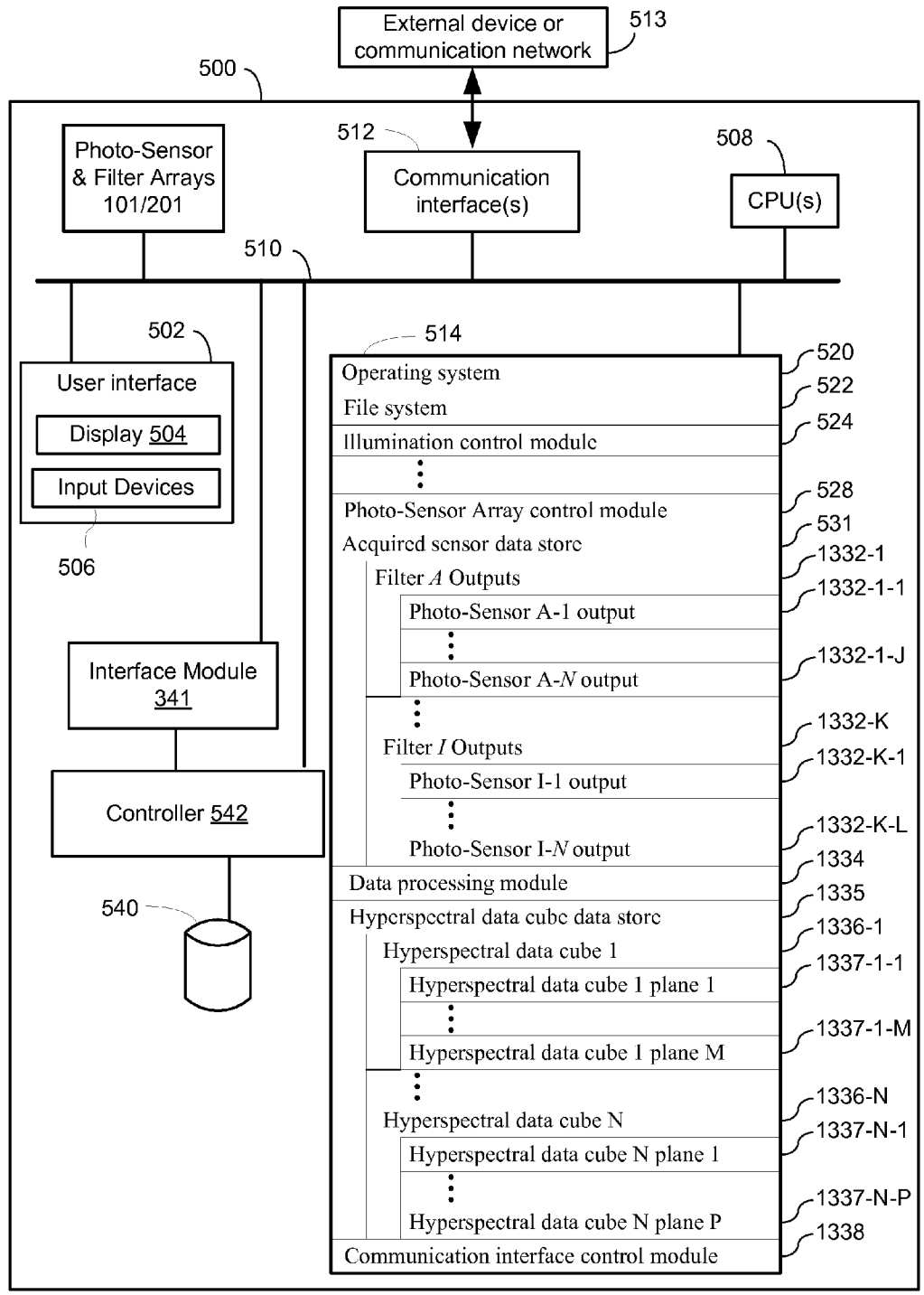
FIG. 5 is a block diagram of an implementation of a hyperspectral imaging device in accordance with some embodiments of the present disclosure.

FIG. 4, in conjunction with FIG. 5, illustrates an advantage of the spectral images used in one embodiment of the present disclosure. A single exposure of light 21 from a lens assembly is filtered by filter array 201 to form filtered light 31 that impinges upon sensor 101 and, from this single exposure, multiple images 1332 of the same region 280 of a patient are concurrently made. FIG. 4 illustrates a hyperspectral imaging device 132/142/232 comprising a photo-sensor array 101 including a plurality of photo-sensors 111. Each photo-sensor 111 provides a respective output. Hyperspectral imaging device 132/142/232 further comprises a spectral filter array 201 having a plurality of filter elements 211. Each filter element 211 is arranged to filter light 21 received by a respective one or more of the plurality of photo-sensors 111. Each filter element 211 is one of a plurality of filter-types. For instance, in FIG. 4, each filter element 211 is one of filter types A, B, C, D, E, F, G, H, and I, with each respective filter-type characterized by a spectral pass-band different from the other filter-types. An interface module selects one or more subsets of photo-sensor 111 outputs. Each subset of photo-sensor 111 outputs is associated with (receives light exclusively through) a single respective filter-type. For instance, in one such subset are the photo-sensors 111 that are associated with (receive light exclusively from) filter type A, another such subset are the photo-sensors 111 that are associated with filter type B and so forth. A control module is configured to generate a hyperspectral data cube 1336 from the one or more sub-sets of photo-sensor outputs by generating a plurality of respective images 1337. In some embodiments, each respective image 1337 in the plurality of images is produced from a single respective sub-set of photo-sensor outputs 111 so that each respective image 1337 in the plurality of images is associated with a particular filter-type. Thus, for example, referring to FIG. 4, all the photo-sensors 111 that receive filtered light from filter elements 211 of filter type A are used to form a first image 1337-1, all the photo-sensors 111 that receive filtered light from filter elements 211 of filter type B are used to form a second image 1337-2, all the photo-sensors 111 that receive filtered light from filter elements 211 of filter type C are used to form a third image 1337-3, and so forth thereby creating a hyperspectral data cube 1336 from the one or more sub-sets of photo-sensor outputs. The hyperspectral data cube 1336 comprises the plurality of images, each image being of the same region of a subject but at a different wavelength or wavelength ranges.

The concept disclosed in FIG. 4 is highly advantageous because multiple light exposures do not need to be used to acquire all the images 1337 needed to form the hyperspectral data cube 1336. In some embodiments, a single light exposure is used to concurrently acquire each image 1337. This is made possible because the spatial resolution of the sensor 101 exceeds the resolution necessary for an image 1337. Thus, rather than using all the pixels in the sensor 101 to form each image 1337, the pixels can be divided up in the manner illustrated in FIG. 4, for example, using filter plate 201 so that all the images are taken concurrently.

In some implementations, the spectral pass-bands of the filter-elements used in a filter array 201 correspond to a set of narrow spectral ranges used to identify a particular type of spectral signature in an object (e.g., in a tissue of a subject). In one implementation, an imaging device comprises a filter array 201 containing a first set of filter elements sufficient to distinguish spectral signatures related to a first medical condition (e.g., a pressure ulcer) from healthy tissue (e.g., non-ulcerated tissue). In one implementation, the filter array 201 of the imaging device further contains a second set of filter elements sufficient to distinguish spectral signatures related to a second medical condition (e.g., a cancerous tissue) from healthy tissue (e.g., a non-cancerous tissue). In some implementations, the first set of filter elements and the second set of filter elements may overlap, such that a particular filter element is used for investigation of both types of medical conditions. Accordingly, in some implementations, the imaging device will have a plurality of imaging modalities, each individual imaging modality related to the investigation of a different medical condition.

In some embodiments, each respective image 1337 of the plurality of images is generated by applying an interpolation process to the respective subset of photo-sensor outputs for the one respective filter-type corresponding to the respective image. Such interpolation processes are known in the art.

As with light sources, filter elements 211 can be described in terms of their spectral "bandpass," e.g., the span of component wavelengths allowed to pass through the filter. In some implementations, the bandpass of a filter element 211 is defined as the span of component wavelengths at which the filter 211 is at least half as transparent as compared to the characteristic or center wavelength (FWHM). For example, the spectral bandpass of a filter element 211 that is 100% transparent with respect to at least one component wavelength is the span of consecutive component wavelengths at which the filter element is at least 50% transparent. In certain implementations, the bandpass of a filter element 211 can be equivalently expressed in terms of the component wavelengths (e.g., 450-480 nm) or as the width of the bandpass at the central wavelength (e.g., 30 nm at 465 nm or ±15 nm at 465 nm).

A bandpass filter of a filter element 211 can also be described in terms of its "characteristic wavelength," e.g., the wavelength at which the filter is most transparent, or its "center wavelength," e.g., the component wavelength at the midpoint of the spectral bandpass. In certain implementations, the bandpass filter is characterized by both its characteristic or center wavelength and its spectral bandwidth. For example, a bandpass filter with a center wavelength of 340±2 nm, a FWHM bandwidth of 10±2, and a peak transmission (e.g., the maximum percentage transmission within the passband) of 50%, allows at least 25% of each component light having a wavelength from 330±4 nm to 350±4 nm to pass through.

In specific implementations, a filter element 211 is a bandpass filter, e.g., a filter that allows only radiation having a wavelength in a certain range to pass, while blocking passage of other wavelengths. In certain embodiments, the FWHM spectral bandpass of a filter element 211 (e.g., the size of the passband transmitted through the filter) is no more than about 100 nm, preferably no more than about 50 nm, more preferably no more than about 25 nm. In yet other embodiments, the FWHM spectral bandwidth of a filter element 211 is no more than 250 nm, 200 nm, 200 nm, 175 nm, 150 nm, 150 nm, 125 nm, 100 nm, 90 nm, 80 nm, 75 nm, 70 nm, 65 nm, 60 nm, 55 nm, 50 nm, 45 nm, 40 nm, 35 nm, 30 nm, 25 nm, 20 nm, 15 nm, 10 nm, 9 nm, 8 nm, 7 nm, 6 nm, 5 nm, 4 nm, 3 nm, 2 nm, or 1 nm.

In certain implementations, the bandpass filter of a filter element 211 is a narrow pass filter. In specific implementations, the narrow pass filter has a FWHM spectral bandwidth of no more than 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, 9 nm, 8 nm, 7 nm, 6 nm, 5 nm, 4 nm, 3 nm, 2 nm, or 1 nm.

In some implementations, the filter elements 211, for instance those illustrated in FIG. 4, are plurality of bandpass illumination filters having central wavelengths that are separated by at least 10 nm, or at least 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, or more.

FIG. 5 is a block diagram of an implementation of a hyperspectral imaging device, such as device 132/142/232 (hereinafter referred to as "imaging device 500" for brevity). In particular FIG. 5 is not limited to the single sensor embodiments described with respect to FIGS. 1 through 4. In fact, FIG. 5 encompasses any form of hyperspectral imaging device provided that the imaging data is processed in accordance with the methods described in more detail below, in conjunction with FIG. 7.

The methods described herein can be employed with any known hyperspectral/multispectral imaging system. For example, in one embodiment, the methods described herein are employed in conjunction with a spatial scanning HSI system. Spatial scanning HSI systems include point scanning and line-scanning imaging systems in which a complete spectrum is simultaneously acquired at a single pixel or line of pixels. The instrument then scans through a region of interest collecting complete spectrums at each point (e.g., pixel) or line (e.g., line of pixels) sequentially. In another embodiment, the methods described herein are employed in conjunction with a spectral scanning HSI system. Spectral scanning HSI systems acquire an image of the entire region of interest at a single wavelength with a two-dimensional detector. The instrument then steps through a series of wavelengths, sequentially collecting images of the entire region of interest at each wavelength.

As such, FIG. 5 encompasses a broad range of hyperspectral imaging devices, provided they are modified, or otherwise adapted, to process data in the manner disclosed herein. As such, FIG. 5 represents, by way of example and upon adaptation to perform the methods disclosed herein, any of the hyperspectral imaging devices of FIGS. 1 through 4 described above, and/or any of the hyperspectral imaging devices disclosed in U.S. Pat. Nos. 6,640,130; 6,640,132; 6,810,279; 8,175,688; 8,320,996; 8,374,682; 8,224,425; 8,548,570; 8,463,366; 8,655,433, International Publications Nos. WO 2014/007869 and WO 2013/184226, and International Patent Application No. PCT/US13/65785, International Patent Application filing date Oct. 18, 2013, entitled "Single-Sensor Hyperspectral Imaging Device," each of which is hereby incorporated by reference herein in its entirety. While some example features are illustrated in FIG. 5, those skilled in the art will appreciate from the present disclosure that various other features have not been illustrated for the sake of brevity and so as not to obscure more pertinent aspects of the example implementations disclosed herein. To that end, the imaging device 500 includes one or more central processing units (CPU) 508, an optional main non-volatile storage unit 540, an optional controller 542, a system memory 514 for storing system control programs, data, and application programs, including programs and data optionally loaded from the non-volatile storage unit 540. In some implementations the non-volatile storage unit 540 includes a memory card, for storing software and data. The storage unit 540 is optionally controlled by the controller 542.

In some implementations, the imaging device 500 optionally includes a user interface 502 including one or more input devices 506 (e.g., a touch screen, buttons, or switches) and/or an optional display 504. Additionally and/or alternatively, in some implementations, the imaging device 500 may be controlled by an external device such as a handheld device, a smartphone (or the like), a tablet computer, a laptop computer, a desktop computer, and/or a server system. To that end, the imaging device 500 includes one or more communication interfaces 512 for connecting to any wired or wireless external device or communication network (e.g., a wide area network such as the Internet) 513. In some embodiments imaging device 500 is very compact and docks directly onto or with a handheld device, a smartphone (or the like), a tablet computer, and/or a laptop computer by an eletronic interface. The imaging device 500 includes an internal bus 510 for interconnecting the aforementioned elements. The communication bus 510 may include circuitry (sometimes called a chipset) that interconnects and controls communications between the aforementioned components.

In some implementations, the imaging device 500 communicates with a communication network 513, thereby enabling the imaging device 500 to transmit and/or receive data between mobile communication devices over the communication network, particularly one involving a wireless link, such as cellular, WiFi, ZigBee, BlueTooth, IEEE 802.11b, 802.11a, 802.11g, or 802.11n, etc. The communication network can be any suitable communication network configured to support data transmissions. Suitable communication networks include, but are not limited to, cellular networks, wide area networks (WANs), local area networks (LANs), the Internet, IEEE 802.11b, 802.11a, 802.11g, or 802.11n wireless networks, landline, cable line, fiber-optic line, etc. The imaging system, depending on an embodiment or desired functionality, can work completely offline by virtue of its own computing power, on a network by sending raw or partially processed data, or both concurrently.

The system memory 514 includes high-speed random access memory, such as DRAM, SRAM, DDR RAM, or other random access solid state memory devices; and typically includes non-volatile memory flash memory devices, or other non-transitory solid state storage devices. The system memory 514 optionally includes one or more storage devices remotely located from the CPU(s) 508. The system memory 514, or alternately the non-transitory memory device(s) within system memory 514, comprises a non-transitory computer readable storage medium.

In some implementations, operation of the imaging device 500 is controlled primarily by an operating system 520, which is executed by the CPU 508. The operating system 320 can be stored in the system memory 514 and/or storage unit 540. In some embodiments, the image device 500 is not controlled by an operating system, but rather by some other suitable combination of hardware, firmware and software.

In some implementations, the system memory 514 includes one or more of a file system 522 for controlling access to the various files and data structures described herein, an illumination software control module 524 for controlling a light source associated and/or integrated with the imaging device 500, a photo-sensor array software control module 528, a sensor data store 531 for storing sensor data 1332 acquired by hyperspectral photosensors (e.g. the photo-sensor array 101/201), a data processing software module 1334 for manipulating the acquired sensor data, a hyperspectral data cube data store 1335 for storing hyperspectral data cube data 1336 assembled from the acquired sensor, and a communication interface software control module 1338 for controlling the communication interface 512 that connects to an external device (e.g., a handheld device, laptop computer, or desktop computer) and/or communication network (e.g., a wide area network such as the Internet).

In some nonlimiting exemplary implementations, the acquired sensor data 1332 is arranged and stored by the filter-type associated with each photo-sensor 111 in the photo-sensor array 101. For example, as illustrated in FIG. 4, the photo-sensor output data 1332-1 from the photo-sensors associated with filter-type A are selectable from the photo-sensor output data, such as photo-sensor output data 1332-K associated with filter-type I.

The acquired sensor data 1332 and hyperspectral data cube data 1336 can be stored in a storage module in the system memory 514, and do not need to be concurrently present, depending on which stages of the analysis the imaging device 500 has performed at a given time. In some implementations, prior to imaging a subject and after communicating the acquired sensor data or processed data files thereof, the imaging device 500 contains neither acquired sensor data 1332 nor the hyperspectral data cube data 1336. In some implementations, after imaging a subject and after communicating the acquired sensor data or processed data files thereof, the imaging device 500 retains the acquired sensor data 1332 and/or hyperspectral data cube data 1336 for a period of time (e.g., until storage space is needed, for a predetermined amount of time, etc.).

In some implementations, the programs or software modules identified above correspond to sets of instructions for performing a function described above. The sets of instructions can be executed by one or more processors, e.g., a CPU(s) 508. The above identified software modules or programs (e.g., sets of instructions) need not be implemented as separate software programs, procedures, or modules, and thus various subsets of these programs or modules may be combined or otherwise re-arranged in various embodiments. In some embodiments, the system memory 514 stores a subset of the modules and data structures identified above. Furthermore, the system memory 514 may store additional modules and data structures not described above.

The system memory 514 optionally also includes one or more of the following software modules, which are not illustrated in FIG. 5: a spectral library which includes profiles for a plurality of medical conditions, a spectral analyzer software module to compare measured hyperspectral data to a spectral library, control modules for additional sensors, information acquired by one or more additional sensors, an image constructor software module for generating a hyperspectral image, a hyperspectral image assembled based on a hyperspectral data cube and optionally fused with information acquired by an additional sensor, a fusion software control module for integrating data acquired by an additional sensor into a hyperspectral data cube, and a display software control module for controlling a built-in display.

While examining a subject and/or viewing hyperspectral images of the subject, a physician can optionally provide input to the image device 500 that modifies one or more parameters upon which a hyperspectral image and/or diagnostic output is based. In some implementations, this input is provided using input device 506. Among other things, the image device can be controlled to modify the spectral portion selected by a spectral analyzer (e.g., to modify a threshold of analytical sensitivity) or to modify the appearance of the image generated by an image assembler (e.g., to switch from an intensity map to a topological rendering).

In some implementations, the imaging device 500 can be instructed to communicate instructions to an imaging subsystem to modify the sensing properties of one of the photo-sensor array 101 and the filter array 201 (e.g., an exposure setting, a frame rate, an integration rate, or a wavelength to be detected). Other parameters can also be modified. For example, the imaging device 500 can be instructed to obtain a wide-view image of the subject for screening purposes, or to obtain a close-in image of a particular region of interest.

In some implementations, the imaging device 500 does not include a controller 542 or storage unit 540. In some such implementations, the memory 514 and CPU 508 are one or more application-specific integrated circuit chips (ASICs) and/or programmable logic devices (e.g. an FGPA—Filed Programmable Gate Array). For example, in some implementations, an ASIC and/or programmed FPGA includes the instructions of the illumination control module 524, photo-sensor array control module 528, the data processing module 1334 and/or communication interface control module 1338. In some implementations, the ASIC and/or FPGA further includes storage space for the acquired sensor data store 531 and the sensor data 1332 stored therein and/or the hyperspectral data cube data store 1335 and the hyperspectral/multispectral data cubes 1336 stored therein.

In some implementations, the system memory 514 includes a spectral library and a spectral analyzer for comparing hyperspectral data generated by the image device 500 to known spectral patterns associated with various medical conditions. In some implementations, analysis of the acquired hyperspectral data is performed on an external device such as a handheld device, tablet computer, laptop computer, desktop computer, an external server, for example in a cloud computing environment.

In some implementations, a spectral library includes profiles for a plurality of medical conditions, each of which contain a set of spectral characteristics unique to the medical condition. A spectral analyzer uses the spectral characteristics to determine the probability that a region of the subject corresponding to a measured hyperspectral data cube is afflicted with the medical condition. In some implementations, each profile includes additional information about the condition, e.g., information about whether the condition is malignant or benign, options for treatment, etc. In some implementations, each profile includes biological information, e.g., information that is used to modify the detection conditions for subjects of different skin types. In some implementations, the spectral library is stored in a single database. In other implementations, such data is instead stored in a plurality of databases that may or may not all be hosted by the same computer, e.g., on two or more computers addressable by wide area network. In some implementations, the spectral library is electronically stored in the storage unit 540 and recalled using the controller 542 when needed during analysis of hyperspectral data cube data.

In some implementations, the spectral analyzer analyzes a particular spectra derived from hyperspectral data cube data, the spectra having pre-defined spectral ranges (e.g., spectral ranges specific for a particular medical condition), by comparing the spectral characteristics of a pre-determined medical condition to the subject's spectra within the defined spectral ranges. In some implementations, the pre-defined spectral ranges correspond to values of one or more of deoxyhemoglobin levels, oxyhemoglobin levels, total hemoglobin levels, oxygen saturation, oxygen perfusion, hydration levels, total hematocrit levels, melanin levels, and collagen levels of a tissue on a patient (e.g., an area 280 of the body of a subject 201). Performing such a comparison only within defined spectral ranges can both improve the accuracy of the characterization and reduce the computational power needed to perform such a characterization.

In some implementations, the medical condition is selected from the group consisting of tissue ischemia, ulcer formation, ulcer progression, pressure ulcer formation, pressure ulcer progression, diabetic foot ulcer formation, diabetic foot ulcer progression, venous stasis, venous stasis disease, infection, shock, cardiac decompensation, respiratory insufficiency, hypovolemia, the progression of diabetes, congestive heart failure, sepsis, dehydration, hemorrhage, hypertension, exposure to a chemical or biological agent, and an inflammatory response.

In some implementations, the spectral analyzer identifies a spectral signature within the hyperspectral data cube that corresponds with a medical condition of the patient. In certain implementations, this is accomplished by identifying a pattern of oxidation or hydration in a tissue associated with a tissue of the patient. In some implementations, the analysis of the hyperspectral data cube includes performing at least one of adjusting the brightness of at least one of the respective digital images in the hyperspectral data cube (e.g., image 1337-1-N at wavelength range No. N), adjusting the contrast of at least one of the respective digital images in the hyperspectral data cube, removing an artifact from at least one of the respective digital images in the hyperspectral data cube, processing one or more sub-pixels of at least one of the respective digital images in the hyperspectral data cube, and transforming a spectral hypercube assembled from a plurality of digital images.

In some implementations, the display 504 which receives an image (e.g., a color image, mono-wavelength image, or hyperspectral/multispectral image) from a display control module, and displays the image. Optionally, the display subsystem also displays a legend that contains additional information. For example, the legend can display information indicating the probability that a region has a particular medical condition, a category of the condition, a probable age of the condition, the boundary of the condition, information about treatment of the condition, information indicating possible new areas of interest for examination, and/or information indicating possible new information that could be useful to obtain a diagnosis, e.g., another test or another spectral area that could be analyzed.

In some implementations, a housing display is built into the housing of the imaging device 500. In an example of such an implementation, a video display in electronic communication with the processor 508 is included. In some implementations, the housing display is a touchscreen display that is used to manipulate the displayed image and/or control the image device 500.

In some implementations, the communication interface 512 comprises a docking station for a mobile device having a mobile device display. A mobile device, such as a smart phone, a personal digital assistant (PDA), an enterprise digital assistant, a tablet computer, an IPOD, a digital camera, or a portable music player, can be connected to the docking station, effectively mounting the mobile device display onto the imaging device 500. Optionally, the mobile device is used to manipulate the displayed image and/or control the image device 500.

In some implementations, the imaging device 500 is configured to be in wired or wireless communication with an external display, for example, on a handheld device, tablet computer, laptop computer, desktop computer, television, IPOD, or projector unit, on which the image is displayed. Optionally, a user interface on the external device is used to manipulate the displayed image and/or control the imaging device 500.

In some implementations, an image can be displayed in real time on the display. The real-time image can be used, for example, to focus an image of the subject, to select an appropriate region of interest, and to zoom the image of the subject in or out. In one embodiment, the real-time image of the subject is a color image captured by an optical detector that is not covered by a detector filter. In some implementations, the imager subsystem comprises an optical detector dedicated to capturing true color images of a subject. In some implementations, the real-time image of the subject is a monowavelength, or narrow-band (e.g., 10-50 nm), image captured by an optical detector covered by a detector filter. In these embodiments, any optical detector covered by a detector filter in the imager subsystem may be used for: (i) resolving digital images of the subject for integration into a hyperspectral data cube, and (ii) resolving narrow-band images for focusing, or otherwise manipulating the optical properties of the imaging device 500.

In some implementations, a hyperspectral image constructed from data collected by the photo-sensor array 101 is displayed on an internal housing display, mounted housing display, or external display. Assembled hyperspectral data (e.g., present in a hyperspectral/multispectral data cube) is used to create a two-dimensional representation of the imaged object or subject, based on one or more parameters. An image constructor module, stored in the imaging system memory or in an external device, constructs an image based on, for example, an analyzed spectra. Specifically, the image constructor creates a representation of information within the spectra. In one example, the image constructor constructs a two-dimensional intensity map in which the spatially-varying intensity of one or more particular wavelengths (or wavelength ranges) within the spectra is represented by a corresponding spatially varying intensity of a visible marker.

In some implementations, the image constructor fuses a hyperspectral image with information obtained from one or more additional sensors. Non-limiting examples of suitable image fusion methods include: band overlay, high-pass filtering method, intensity hue-saturation, principle component analysis, and discrete wavelet transform.

FIG. 6 is a schematic illustration of a hyperspectral data cube 1336. Hyperspectral sensors collect information as a set of images, which are referred to herein as hyperspectral data cube planes 1337. Each image 1337 represents a range of the electromagnetic spectrum and is also known as a spectral band. These 'images' 1337 are then combined and form a three-dimensional hyperspectral data cube 1336 for processing and analysis.

Figure 7A:
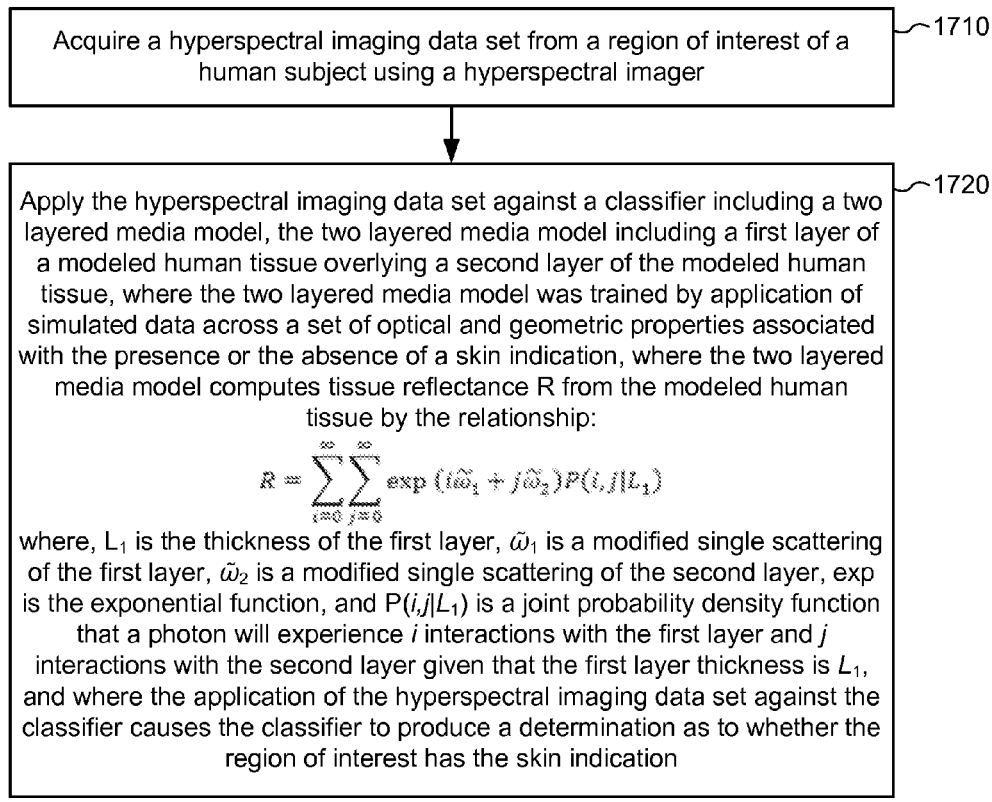
FIG. 7A is a flowchart representation of an implementation of a method of applying a hyperspectral imaging data set against a classifier comprising a two layered media model in accordance with a first aspect of the present disclosure.
Figure 9:
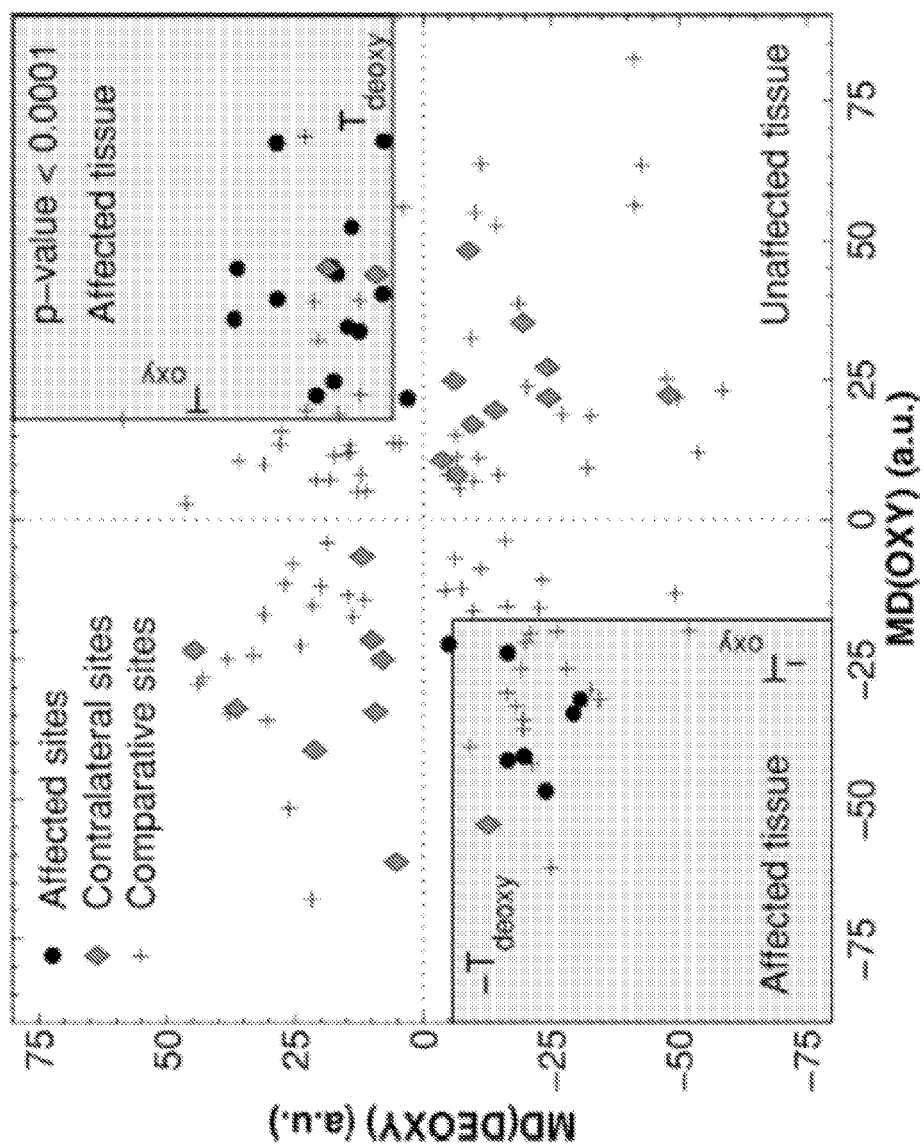
FIG. 9 illustrates a scatter plot showing values of MD(OXY) and MD(DEOXY) determined for 21 affected and 21 contralateral sites from diabetic subjects who developed foot ulcers and from diabetic subjects in the comparative groups. Values from affected areas were found to fall inside the gray regions where |MD(OXY)|>18 and |MD (DEOXY)|>5.8 with a p-value of <0.0001. Data from contralateral sites were presented for reference and not to serve as a control.
Figure 10:
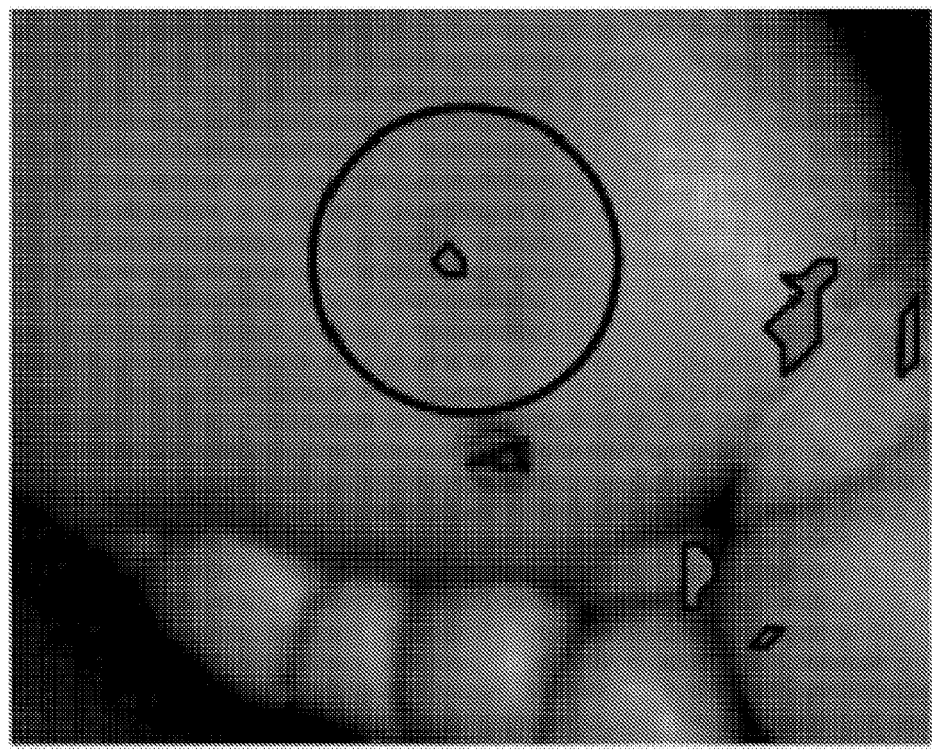
FIG. 10 illustrates a composite image corresponding to FIG. 8B, where the polygon overlays indicate that the maximum differences in oxyhemoglobin and deoxyhemoglobin are such that |MD(OXY)|>18 and |MD (DEOXY)|>5.8, where the approximate location of subsequence ulceration depicted in FIG. 8B is circles.
Figure 11:
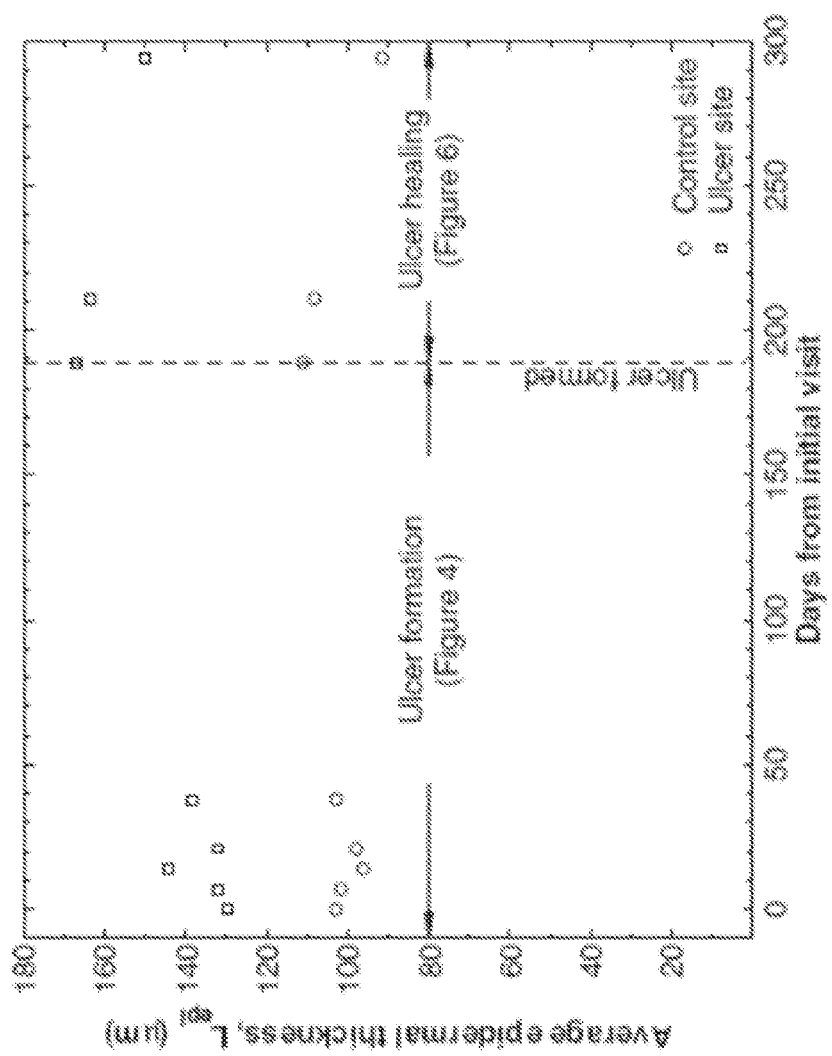
FIG. 11 shows average retrieved epidermal thickness as a function of days from the first visit on Jun. 27, 2007 (visit 1) to May 27, 2008 (visit 6) calculated at the preulcer site (square) and at the control site (circle) for an examined foot.

FIGS. 7A, 7B and 7C provide respective flowchart representations of methods for applying a hyperspectral imaging data set acquired using the above-identified imagers against a classifier comprising a two layered media model associated in accordance with embodiments of the present disclosure. In particular, FIGS. 7A, 7B and 7C illustrate a methods that are used to process hyperspectral data cube 1336 by, for example data processing module 1334 or some other program associated with, or that uses the hyperspectral data cube 1336 data from, hyperspectral imager 500.

A model of light transfer through two layered media resembling organic tissue is disclosed whereby the top and bottom layers represent the epithelium and connective tissue, respectively. Tissue reflectance R will be modeled according to an extended modified Beer-Lambert's law. The modified Beer-Lambert's is stated as $$R = \exp(L(\mu_s') \cdot \mu_a \cdot \log 10)$$ Equation 1 where $L(\mu_s')$ is the effective average path-length of light through homogenous tissue, and $\mu_a(\lambda)$ and $\mu_s'(\lambda)$ are the absorption and reduced scattering coefficients of the skin, respectively. This model is deficient primarily in its inability to model light transfer in two layered media such as skin. Instead, we presented an extended modified Beer-Lambert's law for two layered media $$R = \sum_{i=0}^{\infty} \sum_{j=0}^{\infty} \exp(i\tilde{\omega}_1 + j\tilde{\omega}_2) P(i, j | L_1)$$ Equation 2 where $L_1$ is the thickness of the top (first) layer, $\tilde{\omega}_1$ and $\tilde{\omega}_2$ are the modified single scattering of the first and second layer (See Equation 17), respectively, exp is the exponential function, and $P(i,j|L_1)$ is a joint probability density function that a photon will experience i interactions with layer 1 and j interactions with layer 2 given that the layer 1 thickness is $L_1$.

Accordingly, with reference to FIG. 7A, one aspect of the present disclosure provides a computer implemented method, performed by a computer system having one or more processors and memory storing one or more programs for execution by the one or more processors, the method comprising acquiring (1710) a hyperspectral imaging data set from a region of interest of a human subject using a hyperspectral imager. Then, the hyperspectral imaging data set is applied (1720) against a classifier comprising a two layered media model. The two layered media model comprising a first layer of a modeled human tissue overlying a second layer of the modeled human tissue. The two layered media model has been trained by application of simulated data across a set of optical and geometric properties associated with the presence or the absence of a skin indication, where the two layered media model computes tissue reflectance R from the modeled human tissue by the relationship:

$$R = \sum_{i=0}^{\infty} \sum_{j=0}^{\infty} \exp(i\tilde{\omega}_1 + j\tilde{\omega}_2) P(i, j | L_1)$$

Here, $L_1$ is the thickness of the first layer, $\tilde{\omega}_1$ is a modified single scattering of the first layer, $\tilde{\omega}_2$ is a modified single scattering of the second layer, exp is the exponential function, and $P(i,j|L_1)$ is a joint probability density function that a photon will experience i interactions with the first layer and j interactions with the second layer given that the first layer thickness is $L_1$, where the application of the hyperspectral imaging data set against the classifier causes the classifier to produce a determination as to whether the region of interest has the skin indication.

Some embodiments of the method presented here are based on Monte Carlo (MC) simulations which are commonly used in modeling light transfer through multi-layered tissue. A complete description of Monte Carlo simulation is given in reference MCML-001, which is hereby incorporated by reference herein in its entirety for such purpose. In short, the solution of radiative transfer equation is approximated by simulating the propagation of virtual photons through simulated tissue with given optical properties. The accuracy of the solution increases when more photons are simulated. Typically, MC cannot be used in industrial biophotonics systems because performing a single simulation can take minutes or days.

Instead, scaled or white MC (wMC) can be implemented whereby a single simulation is performed for a set of optical and geometric properties and the trajectory of each of millions of photons recorded in a database (see Reference wMC-001). Then, the database can be used to calculate the reflectance of tissue for different optical properties by applying a proper transformation. The innovation described below stores the photon database in a computationally and space-efficient way. It also expands traditional wMC to two model light transfer in two layered media.

For the instant disclosure software was written based on a known Monte Carlo Modeling of light transport in multi-layered tissues algorithm, but modified to record the locations of photon-media interaction and calculate $P(i,j|L_1)$.

Simulated Photon Trajectory.

The software calculated trajectory vector $\vec{x}_p$ for each photon p such that $\vec{x}_{p,k} = \langle x, y, z \rangle_k$, represents the location of the $k^{th}$ interaction between the photon and the medium (the two layer model). A simulation was set up with geometry given in AO-001, FIG. 1 "Semi-Infinite Medium," which is hereby incorporated by reference. For this master simulation, the absorption coefficient, scattering coefficient, index of refraction, and Henyey-Greenstien asymmetry factor were set to $\mu_a = 0$ cm$^{-1}$, $\mu_s = 1$ cm$^{-1}$, n=1.44, and g=0. Because the medium was simulated to have no absorption ($\mu_a = 0$), simulated photons propagated and scattered until they were emitted into the atmosphere. The trajectory vector $\vec{x}_{p,k} = \langle x, y, z \rangle_k$ was stored in a non-transitory data file for each of 10,000,000 simulated photons.

Extending to Non-Absorbing but Two Layer Case.

The database described above can be used to approximate $P(i,j|L_1)$ for a simplified two layer geometry of type in AO-001, FIG. 1 entitled "Two Layer Medium", which is hereby incorporated by reference herein, but with $\mu_{a,1} = \mu_{a,2} = 0$ cm$^{-1}$ and $\mu_{s,1} = \mu_{s,2} = 1$ cm$^{-1}$ and with top layer thickness $L_1$. Let $N_{p,1}$ and $N_{p,2}$ represent the number of interactions between photon p and layers 1 and 2, respectively. Then, $$N_{p,1} = \sum_{\vec{x}_{p,k}} \begin{cases} 1 & \vec{x}_{p,k} \cdot \langle 0, 0, 1 \rangle < L_1 \\ 0 & \vec{x}_{p,k} \cdot \langle 0, 0, 1 \rangle \geq L_1 \end{cases} \quad \text{Equation 3}$$

where "·" represents the dot product and $\vec{x}_{p,k} \cdot \langle 0,0,1 \rangle$ is simply the "z" element of $\vec{x}_{p,k}$. Likewise, $$N_{p,2} = \sum_{\vec{x}_{p,k}} \begin{cases} 0 & \vec{x}_{p,k} \cdot \langle 0, 0, 1 \rangle < L_1 \\ 1 & \vec{x}_{p,k} \cdot \langle 0, 0, 1 \rangle \geq L_1 \end{cases} \quad \text{Equation 4}$$

Let the function $N(i,j|L_1)$ count the number of photons out of 10,000,000 that experience i interactions with layer 1 and j interactions with layer 2. Then $$N(i,j|L_1) = \sum_{p=1}^{p=P} \begin{cases} 1 & N_{p,1} = i \text{ and } N_{p,2} = j \\ 0 & \text{othewise} \end{cases} \quad \text{Equation 5}$$

where P is the number of photons in the simulation. Then, the joint probability density function $P(i,j|L_1)$ can be estimated as $$P(i,j|L_1) \approx \frac{N(i,j|L_1)}{P} \quad \text{Equation 6}$$

As P becomes arbitrarily large, Equation 6 approaches equality. Depending on the application, P may be increased so as to reduce the estimation error below numerical tolerance.

Extending to Absorbing Two Layer Case with $\mu_{a,1} + \mu_{s,1} = \mu_{a,2} + \mu_{s,2} = 1$.

The interaction of a simulated photon traversing an optical medium is governed by the total interaction coefficient $\mu_t = \mu_a + \mu_s$. The likelihood that a photon will travel a distance s before an interaction occurs can be modeled as $$s = -\frac{\log(1-u)}{\mu_t} \quad \text{Equation 7}$$

where u is a uniform random variable between 0 and 1, $\mu_t$ is the total interaction coefficient between the photon and the tissue, s is the sampled path length, and log represents the natural logarithm function. Note that Equation 7 does not depend on the actual values of $\mu_a$ and $\mu_s$ but only on their sum. In this section, then, it is assumed that the sum is unity: $\mu_t = \mu_{a,1} + \mu_{s,1} = \mu_{a,2} + \mu_{s,2} = 1$ cm$^{-1}$.

Interaction with the medium results in radiative loss of energy to heat and the deflection of the simulated photon into a new propagation direction. If the photon arrives at an interaction point with energy W, then the total energy deposited is $dW = W\mu_a/\mu_t$ where $\mu_a$ is the local absorption coefficient. The energy remaining in the photon is $$W_{new} = W - dW = W\left(1 - \frac{\mu_a}{\mu_t}\right) = \omega W \quad \text{Equation 8}$$

where $\omega$ is known as the single scattering albedo. The photon will interact with the optical medium—being absorbed and scattered—until it is emitted from the tissue toward a detector such as an optical probe or camera. For the case of two layered media, the amount of energy lost per interaction depends on depth of interaction (i.e., layer 1 or layer 2). Let a photon interact three times with layer 1, twice with layer 2, and then again twice with layer 1 before being reflected. The total energy lost by the photon is $$W_{reflected} = W_0(\omega_1)^3(\omega_2)^2(\omega_1)^2 = W_0(\omega_1)^5(\omega_2)^2 \quad \text{Equation 9}$$

Equation 9 illustrates that the order of interaction is immaterial and only the number of interactions between a simulated photon and a layer is important. In fact, the total energy remitted by P photons can be written compactly as $$W_{total} = W_0 \sum_{i=0}^{\infty} \sum_{j=0}^{\infty} (\omega_1)^i (\omega_2)^j N(i,j|L_1) \qquad \text{Equation 10}$$

where $W_0$ is the initial energy of each photon, $\omega_1$ and $\omega_2$ are the single scattering albedos of the two layers, and $N(i,j|L_1)$ is defined above as the number of photons that interacted with layer 1 and 2 i and j times, respectively. In some embodiments, the total reflectance is calculated as $$R = \frac{W_{total}}{P} = W_0 \sum_{i=0}^{\infty} \sum_{j=0}^{\infty} (\omega_1)^i (\omega_2)^j P(i,j|L_1) \qquad \text{Equation 11}$$

Because it was assumed that $\mu_t=1$ cm$^{-1}$ for both layers, $P(i,j|L_1)$ in Equation 11 can be used as defined in Equation 6.

Thus, making reference to FIG. 7B, another aspect of the present disclosure provides a computer implemented method, performed by a computer system having one or more processors and memory storing one or more programs for execution by the one or more processors. The method comprises acquiring a hyperspectral imaging data set from a region of interest of a human subject using a hyperspectral imager (1730). Then, the hyperspectral imaging data set is applied (1740) against a classifier comprising a two layered media model. The two layered media model comprises a first layer of a modeled human tissue overlying a second layer of the modeled human tissue. The two layered media model has been trained by application of simulated data from a set of photons across a set of optical and geometric properties associated with the presence or the absence of a skin indication. The two layered media model computes tissue reflectance R from the modeled human tissue by the relationship:

$$R = \frac{W_{total}}{P} = W_0 \sum_{i=0}^{\infty} \sum_{j=0}^{\infty} (\omega_1)^i (\omega_2)^j P(i,j|L_1)$$

Here, $W_{total}$ is the total energy remitted by the set of photons, P is the number of photons in the set of photons, $W_0$ is the initial energy of each photon in the set of photons, $\omega_1$ is the single scattering albedo of the first layer, $\omega_2$ is the single scattering albedo of the second layer, $L_1$ is the thickness of the first layer, and $P(i,j|L_1)$ is a joint probability density function that a respective photon in the set of photons will experience i interactions with the first layer and j interactions with the second layer given the first layer thickness $L_1$. The application of the hyperspectral imaging data set against the classifier causes the classifier to produce a determination as to whether the region of interest has the skin indication.

Scaling Parameters when $\mu_{a,1}+\mu_{s,1}\neq 1$

This section relaxes the assumption that $\mu_{a,1}+\mu_{s,1}=1$ cm$^{-1}$. Equation 7 implies an inverse relationship between simulated photon travel distance and total interaction coefficient. In fact, doubling the interaction coefficient $\mu_t$ on average halves the travel distance s. This similarity relationship can be extended to the product of the top layer thickness $L_1$ and total interaction coefficient $\mu_{t,1}$ such that $$P(i,j|L_1,\mu_{a,1},\mu_{s,1}) = P\left(i,j\Big|L_1\mu_{t,1}, \frac{\mu_{a,1}}{\mu_{t,1}}, \frac{\mu_{s,1}}{\mu_{t,1}}\right) \qquad \text{Equation 12}$$

$$= P(i,j|\tilde{L}_1, \tilde{\mu}_{a,1}, \tilde{\mu}_{s,1}, \mu_{t,1}=1)$$

Equation 12 states in words that the likelihood of interaction between a simulated photon and the top layer increases linearly and equally layer thickness and interaction coefficient. The following transformation can then be made:

$$L_1\mu_{t,1} \rightarrow \tilde{L}_1 \qquad \text{Equation 13}$$

$$\frac{\mu_{a,1}}{\mu_{t,1}} \rightarrow \tilde{\mu}_{a,1}$$

$$\frac{\mu_{s,1}}{\mu_{t,1}} \rightarrow \tilde{\mu}_{s,1}$$

$$\mu_{t,1} \rightarrow 1$$

$$\omega_1 \rightarrow \omega_1$$

where "→" indicates equivalence under $P(i,j|L_1)$. Since $\tilde{\mu}_{a,1}+\tilde{\mu}_{s,1}=1$, $P(i,j|\tilde{L}_1,\tilde{\mu}_{a,1},\tilde{\mu}_{s,1})=P(i,j|\tilde{L}_1)$ as defined by Equation 11. Note that the transformation in Equation 12 results in an effective top layer thickness $\tilde{L}_1$ while the single scattering albedo $\omega_1$ is unaltered.

Extending to Absorbing Two Layer Case with $\mu_{a,2}+\mu_{s,2}\neq 1$.

The assumption that $\mu_{a,2}+\mu_{s,2}=1$ can be relaxed by applying the example above to $\mu_{a,2}$ and $\mu_{s,2}$ with the following similarity relationship:

$$\frac{\mu_{a,2}}{\mu_{t,2}} \rightarrow \tilde{\mu}_{a,2} \qquad \text{Equation 14}$$

$$\frac{\mu_{s,2}}{\mu_{t,2}} \rightarrow \tilde{\mu}_{s,2}$$

$$\mu_{t,2} \rightarrow 1$$

$$\omega_2 \rightarrow \omega_2$$

Reference AO-001, hereby incorporated by reference in its entirety, showed that the actual absorption and scattering coefficients of the bottom layer were immaterial to actual reflectance from the medium. In fact, the single scattering albedo $\omega_2$ completely determines the effect of the optical characteristics of the bottom layer on the tissue's reflectance. Then, incorporating the transformations from Equation 12

$$P(i,j|L_1,\mu_{a,1},\mu_{s,1},\mu_{a,2},\mu_{s,2})=P(i,j|\tilde{L}_1,\tilde{\mu}_{a,1},\tilde{\mu}_{s,1},\mu_{t,2}=1,\omega_2) \qquad \text{Equation 15}$$

Since Equation 14 changes $\mu_{t,2}$ to equal 1 cm$^{-1}$ without modifying $\omega_2$ the function $P(i,j|\tilde{L}_1,\tilde{\mu}_{a,1},\tilde{\mu}_{s,1},\mu_{t,2}=1,\omega_2)$ can be written compactly as $P(i,j|\tilde{L}_1)$ and is defined in Equation 11.

Given the above, Equation 11 can be generalized for arbitrary top layer thickness and absorption and scattering coefficients as $$R = \alpha_0 \sum_{i=0}^{\infty} \sum_{j=0}^{\infty} \exp(i\tilde{\omega}_1 + j\tilde{\omega}_2) P(i,j|\tilde{L}_1) \qquad \text{Equation 16}$$

where $$\tilde{\omega}_l = \log \omega_l \qquad \text{Equation 17}$$

Here, the exponential function was used because it is commonly implemented and may be computationally more efficient than the power function $(\omega_l)^i$. However, both implementations are mathematically equivalent. The value $\alpha_0$ was added to account for any other losses such as surface reflectance or the acceptance angle of the optical instrument. Accordingly, referring to FIG. 7C, another aspect of the present disclosures provides a computer implemented method, performed by a computer system having one or more processors and memory storing one or more programs for execution by the one or more processors. The method comprises acquiring (1750) a hyperspectral imaging data set from a region of interest of a human subject using a hyperspectral imager. The hyperspectral imaging data set is applied (1760) against a classifier comprising a two layered media model. The two layered media model comprises a first layer of a modeled human tissue overlying a second layer of the modeled human tissue. The two layered media model has been trained by application of simulated data from a set of photons across a set of optical and geometric properties associated with the presence or the absence of a skin indication. The two layered media model computes tissue reflectance R from the modeled human tissue by the relationship:

$$R = \alpha_0 \sum_{i=0}^{\infty} \sum_{j=0}^{\infty} \exp(i\tilde{\omega}_1 + j\tilde{\omega}_2) P(i,j \mid \tilde{L}_1)$$

Here, $\alpha_0$ is a constant for losses arising from surface reflectance or the acceptance angle of the hyperspectral imager, exp is the exponential function, i is an integer, j is an integer, $\tilde{\omega}_l = \log \omega_l$, $\tilde{\omega}_2 = \log \omega_2$, $\omega_l$ is the single scattering albedo of the first layer, $\omega_2$ is the single scattering albedo of the second layer, $\tilde{L}_1 = L_1 \mu_{t,1}, \mu_{t,1}$ is the total interaction coefficient of the first layer, $L_1$ is the thickness of the top layer, and $P(i,j|L_1)$ is a joint probability density function that a photon in the set of photons will experience i interactions with the first layer and j interactions with the second layer given $\tilde{L}_1$.

Extension to g≠0.

The condition that g=0 can be relaxed. This can be achieved by calculating a joint probability density function $P(i,j|L_1)$ from a master simulation with $\mu_a=0$ cm$^{-1}$, $\mu_s=1$ cm$^{-1}$, n=1.44, and g=0.9 which is a typical value in tissue.

Validation.

This section confirms the accuracy of the present model with respect to MC. First, MC was run for a set of top and bottom layer parameters. Then, Equation 16 was evaluated for the same parameters. The percent difference was calculated to ensure that the accurate and accepted (though slow) MC approach and the novel (and fast) wMC approach produce approximately the same estimate of reflectance from simulated two layer tissue.

Figure 12:
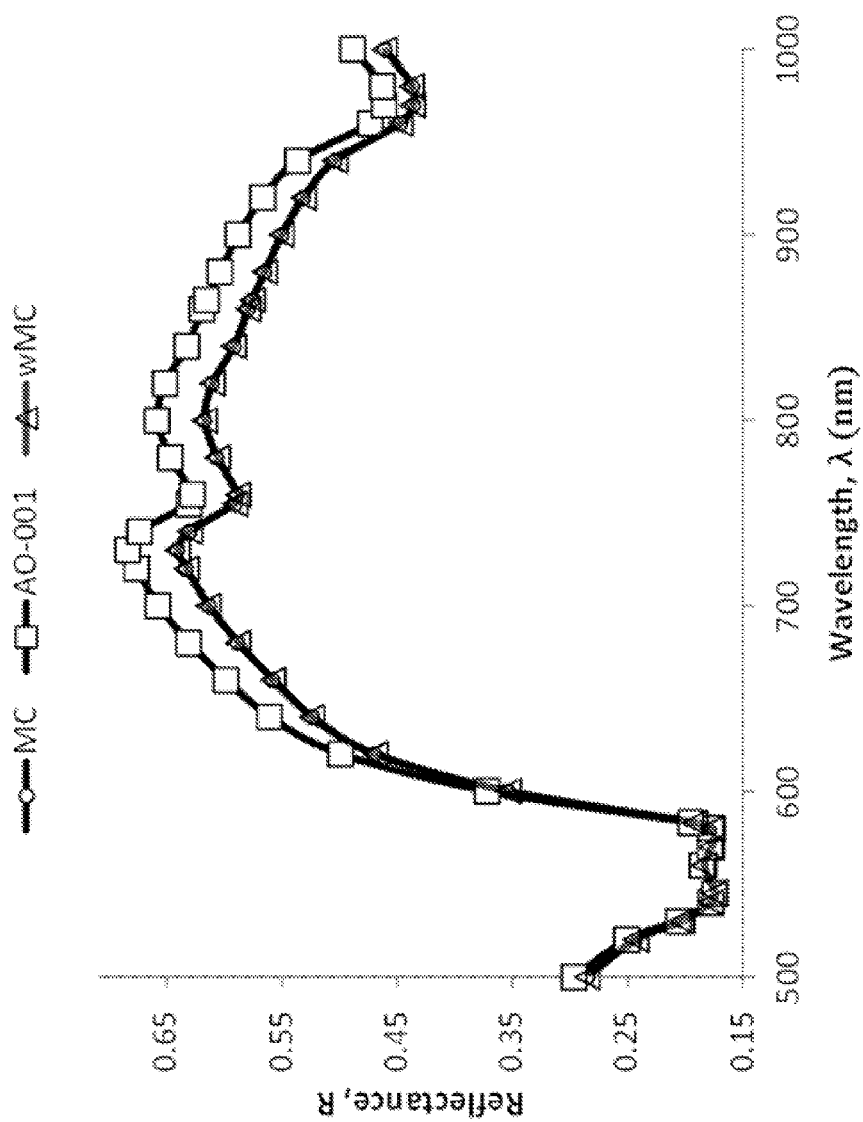
FIG. 12 shows simulated reflectance from two layered tissue oxygen saturation $SO_2$=50%, total hemoglobin concentration $f_{HEME}$=100 μM, melanin concentration $f_{mel}$=0.01 μM, $f_{mel}$=0.01 μM, water concentration $f_{H_2O}$=50%, and epidermal thickness $L_1$=100 μm calculated by the model described in AO-001, wMC, and MC for wavelength λ between 500 and 1000 nm.
Figure 13A:
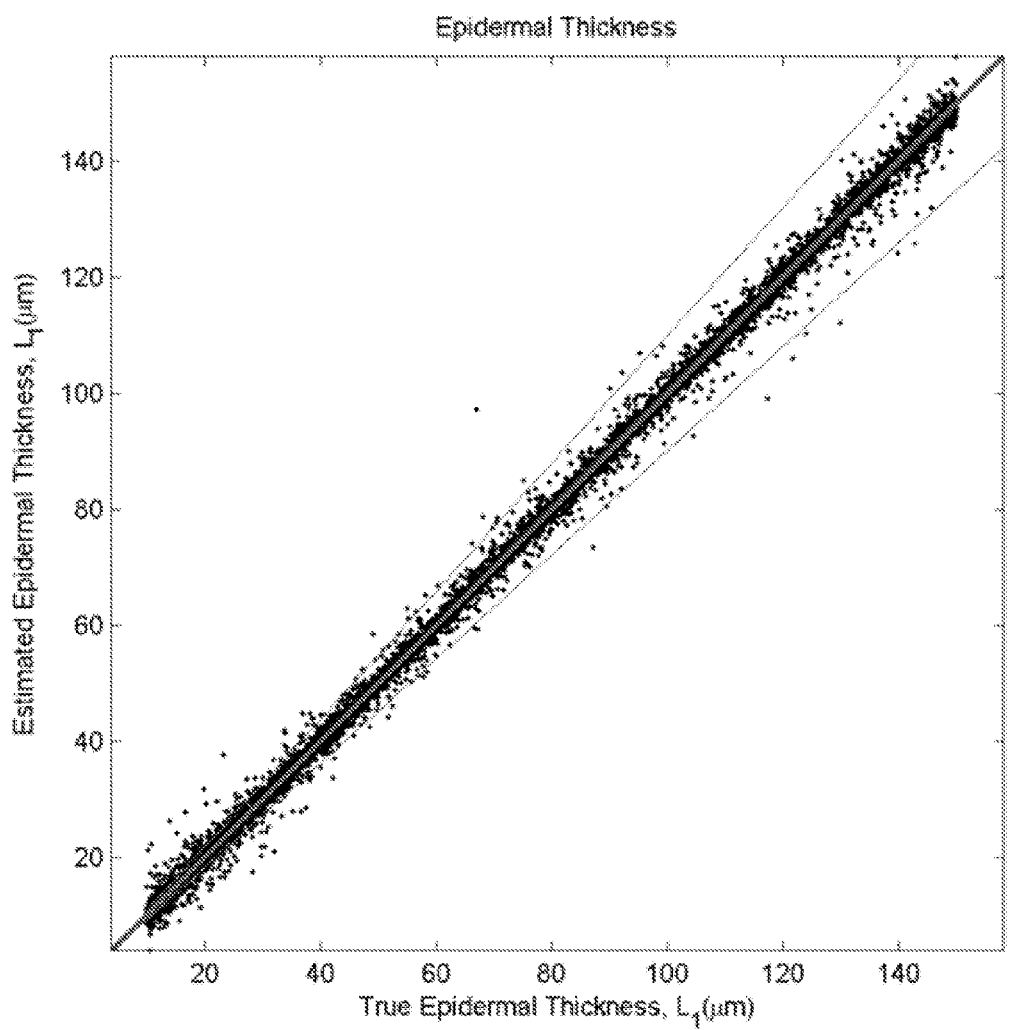
FIGS. 13A and 13B show the input and estimated biometric parameters along with 10% error bounds in accordance with a model of the present disclosure.
Figure 13B:
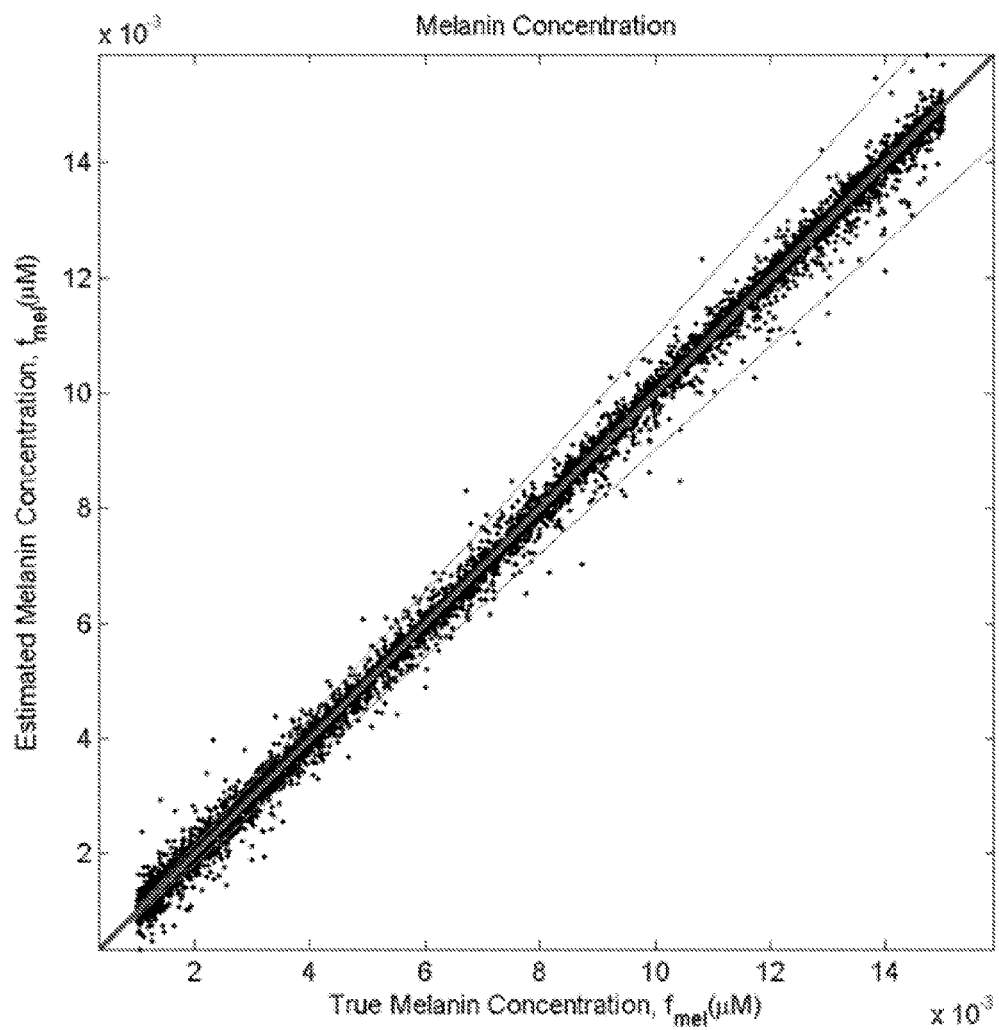
Figure 14A:
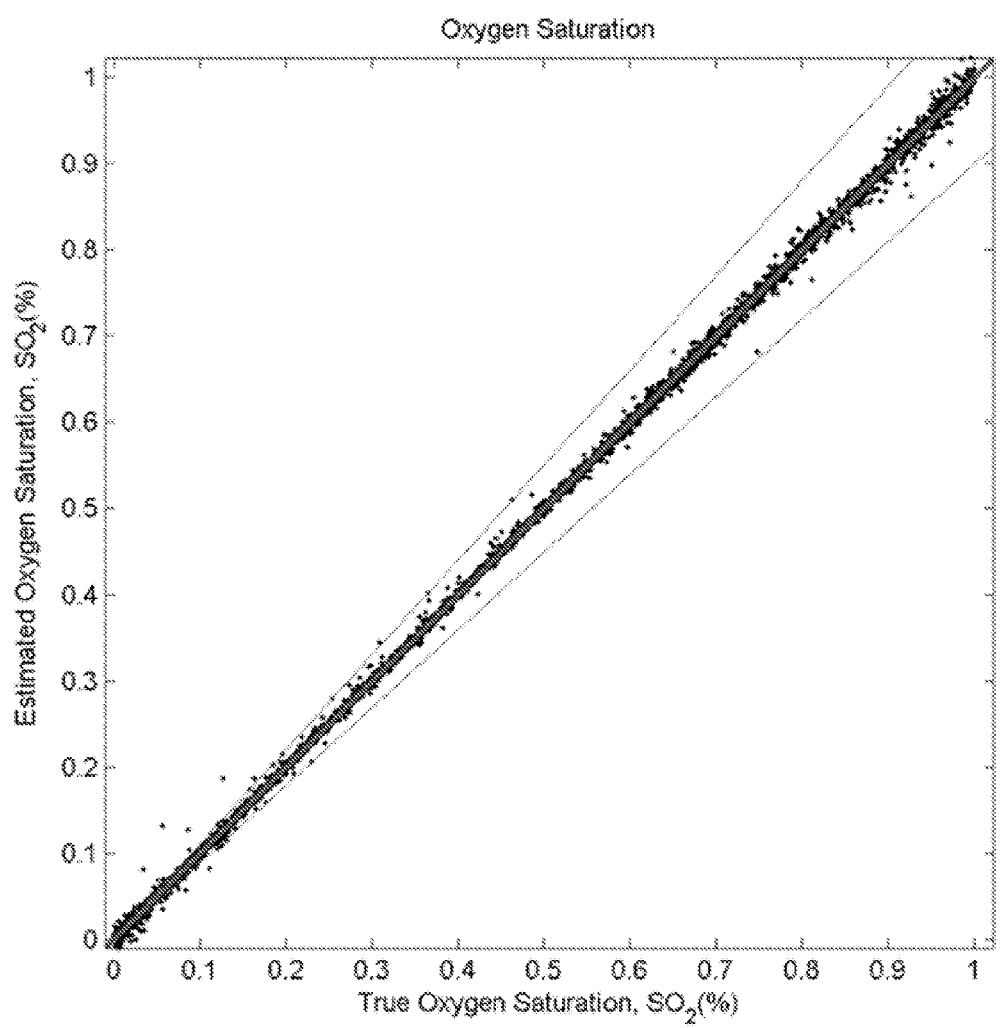
FIGS. 14A and 14B show the input and estimated biometric parameters along with 10% error bounds in accordance with a model of the present disclosure.
Figure 14B:
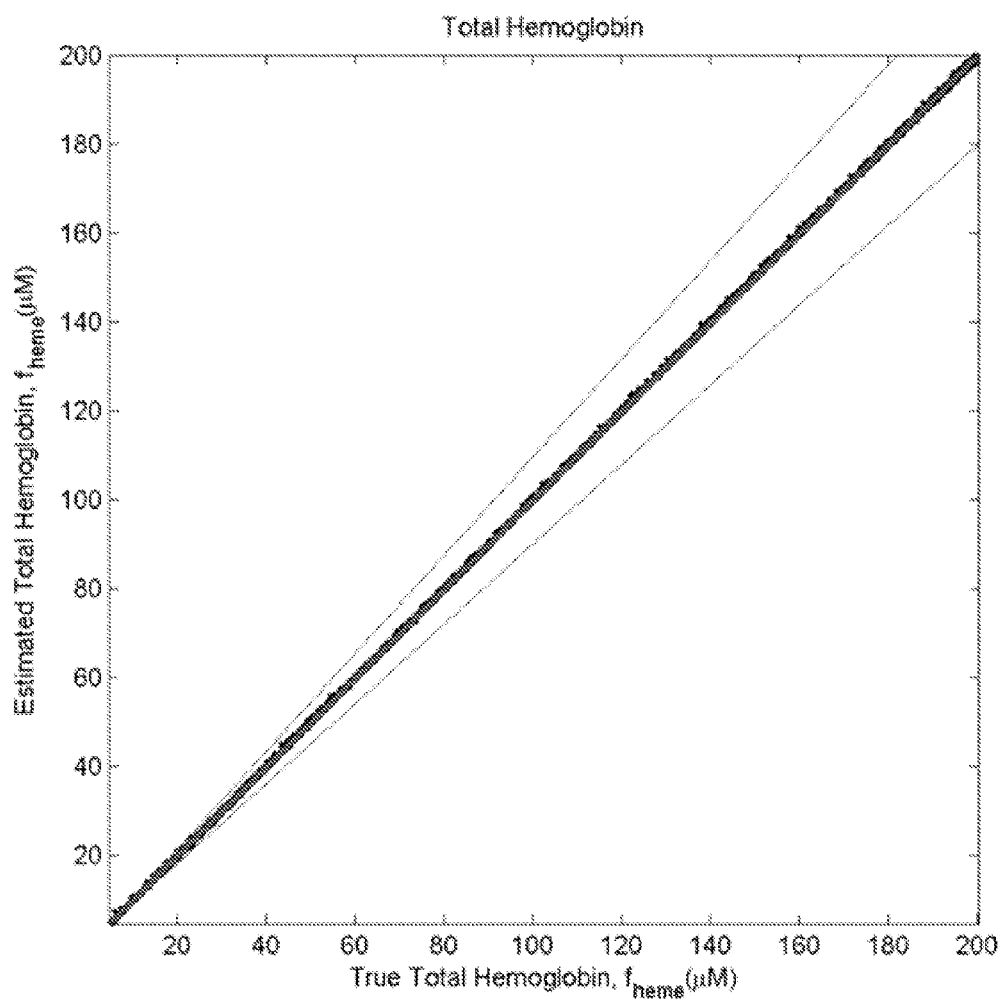
Figure 15:
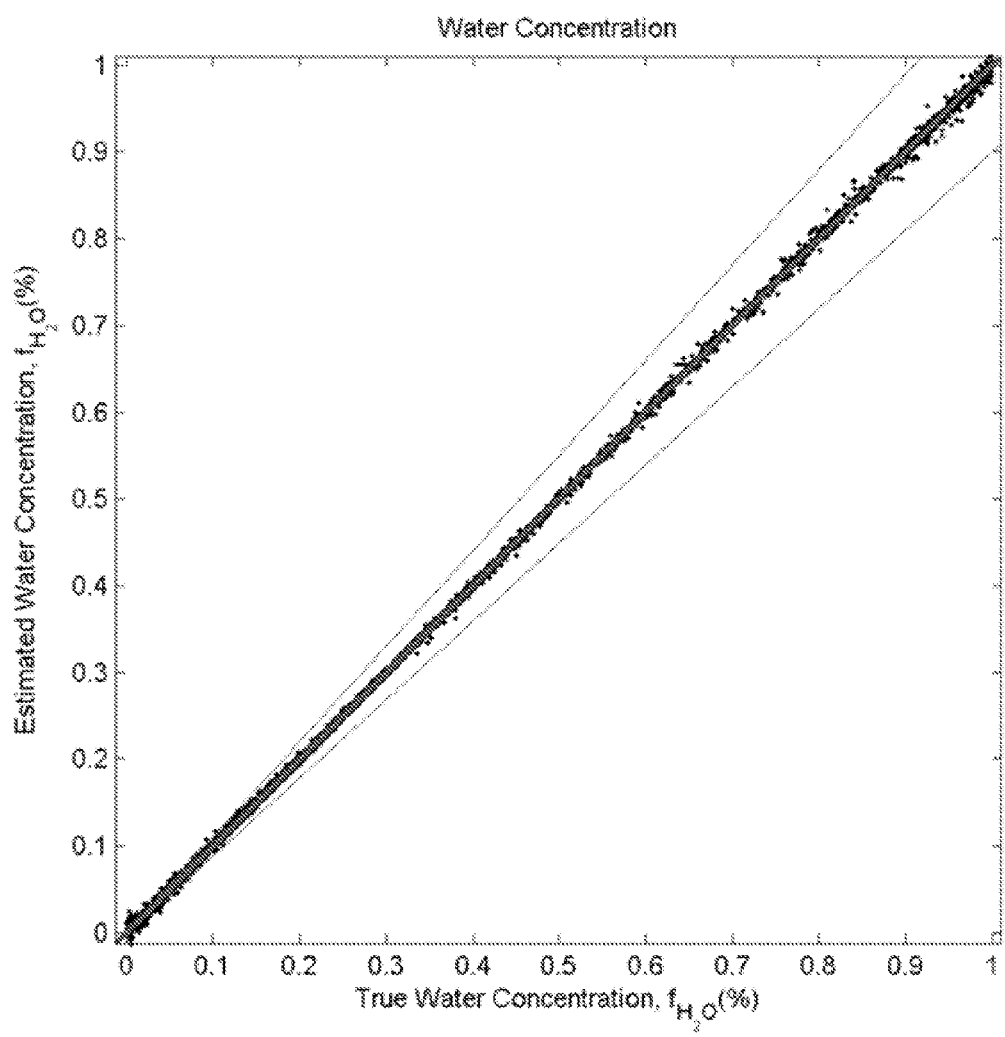
FIG. 15 shows the input and estimated biometric parameters along with 10% error bounds in accordance with a model of the present disclosure.

FIG. 12 shows simulated reflectance from two layered tissue oxygen saturation SO$_2$=50%, total hemoglobin concentration f$_{HEME}$=100 µM, melanin concentration f$_{mel}$=0.01 µM, f$_{mel}$=0.01 µM, water concentration f$_{H_2O}$=50%, and epidermal thickness L$_1$=100 µm calculated by the model described in AO-001, wMC, and MC for wavelength λ between 500 and 1000 nm. It indicates that AO-001 and wMC are almost identical (<1% difference) in the visible range below 600 nm. However AO-001 diverges from MC by more than 10% in the NIR. wMC on the other hand closely follows MC with an error of less than 1% for all wavelengths considered. FIG. 12 indicates that wMC shows greater accuracy than AO-001 in the entire wavelength range of interest to the next generation OxyVu. wMC accurately models the effects of water content and epidermal thickness in the NIR. It shows that the results presented in SPIE-001 and AO-001 can be extended to analysis of NIR reflectance by using the wMC approach disclosed herein.

Application to Tissue Spectroscopy.

This section describes an example of the use of wMC in an inverse sense whereby biometric properties are determined from measured tissue reflectance. Reflectance spectra of skin were simulated using MC. Skin was approximated as a two layer system having a melanin pigmented epidermis and blood pigmented dermis. Multiple simulations were performed for oxygen saturation SO$_2$ between 0% and 100%, total hemoglobin concentration f$_{HEME}$ between 0 and 200 µM, melanin concentration f$_{mel}$ between 0.002 µM and 0.15 µM, water concentration f$_{H_2O}$ between 0 and 100%, and epidermal thickness L$_1$ between 10 µm and 150 µm. Parameters were chosen at random in these range and then $\mu_{a,1}(\lambda)$, $\mu_{s,1}(\lambda)$, $\mu_{a,2}(\lambda)$, and $\mu_{s,2}(\lambda)$ were calculated. MC simulations were performed for each sample with 10,000,000 photons at for λ at 9 wavelengths: 500, 530, 545, 570, 583, 730, 755, 865, and 970 nm.

The inverse problem was solved iteratively according the procedure described in AO-002, Section D, which is hereby incorporated by reference. FIGS. 13A, 13B, 14A, 14B and 15 presents the input and estimated biometric parameters along with 10% error bounds. It indicates that wMC extends the capability of the model described in SPIE-001 and JBP-002 to quantitative analysis of the NIR spectrum.

Machine Learning-Based Inverse Methods

Artificial Neural Networks (ANNs) can be used to efficiently store complex relationships between input and output parameters. The use of ANN in biophotonics is described in detail in the introduction to reference document JBO-002, which is hereby incorporated by reference. A procedure for building an ANN to recognize optical properties of two layered tissue from spatial frequency domain imaging (See References 1 through 3 in JBO-002) is described in JBO-002 Section 3.4, Equation (6), which is hereby incorporated by reference. A similar approach can be used in the context of the disclosed oximetry methods. Using wMC, generate many examples of tissue reflectance from two layer media at the proper wavelength. Train a ANN with the calculated reflectance as an input and the biometric parameters as an output. The ANN constitutes a relationship between measured reflectance and optical properties. This approach circumvents the need for iterative minimization described in the previous section. The ANN approach was tested in this case and produced results almost identical to that presented in FIGS. 13-15.

In some embodiments, $P(i,j|L_1)$ is estimated using an interpolation table to store the reflectance as a function of the 5 parameters of two layered media. This requires substantial memory and some computational resources. Furthermore, the interpolation table would require to be generated for all optical properties to be considered. In some embodiments, a two layer diffusion approximation is used rather than the two layer model.

The inverse method described above can alternatively be accomplished by creating a look up or interpolation table that takes as inputs the reflectance values at the instrument's interrogation wavelengths and produces as outputs the biometric parameters depicted in FIG. 12. In some embodiments, this would require interrogation at six or more wavelengths. The output space would have five values. Thus, a six dimensional interpolation table would have to be created and stored 5 times. In addition, any of the following iterative curve fitting algorithms can be used as well: Newton-Raphson, Levengerb-Marquard, simplex method, gradient projection method, genetic algorithms or other stochastic estimators.

Disclosure of Improved Ulcer Formation Prediction Algorithm

Spatial variation in tissue oxygenation is known to occur at preulcerative sites but may also occur for other reasons unrelated to ulceration. In order to increase the specificity of the ulcer prediction algorithm described in JBO-001, other physiological changes specific to ulceration should be considered. Among these are (i) inflammation of the ulcer and surrounding areas (ii) necrosis (See Ferguson et al., 1996, "The histology of diabetic foot ulcers," *Diabetic Medicine* 13, 30-33; Vande Berg and Rudolph, 1995, "Pressure (decubitus) ulcer: variation in histopathology a light and electron microscope study," *Human Pathology* 26, pp. 195-200; and Witkowski and Parish, 1982, "Histopathology of the decubitus ulcer," *Journal of the American Academy of Dermatology* 6, 1014-1021, each of which is hereby incorporated by reference in its entirety), (iii) callus formation around the ulcer site (Lavery et al., 1998, "Practical criteria for screening patients at high risk for diabetic foot ulceration," Archives of Internal Medicine 158 157-162; Boulton, 2006, "The diabetic foot," Medicine 34, 87-90; Piaggesi et al., 2003, "Semiquantitative analysis of the histopathological features of the neuropathicfoot ulcer," Diabetes Care 26, 3123-3137; and Armstrong and Nguyen, 2000, "Improvement in healing with aggressive edema reduction after debridement of foot infection in persons with diabetes", Archives of Surgery 135, 1405-1409, each of which is hereby incorporated by reference in its entirety), and (iv) loss of the epidermal layer (Vande Berg and Rudolph, 1995, "Pressure (decubitus) ulcer: variation in histopathology a light and electron microscope study", *Human Pathology* 26, 195-200, which is hereby incorporated by reference in its entirety). Inflammation may in turn cause hyper pigmentation due to hemorrhaging of blood into the interstitial fluid and increased melanin production (Valencia et al, 2001, "Chronic venous insufficiency and venous leg ulceration", Journal of the American Academy of Dermatology 44, 401-424; Falanga et al., 1998, "Rapid healing of venous ulcers and lack of clinical rejection with an allogeneic cultured human skin equivalent," Archives of Dermatology 134, 293, 1998; Phillips and Dover, 1991, "Leg ulcers", Journal of the American Academy of Dermatology 25, 965-987; and Sigel et al, 1974, "The epidemiology of lower extremity deep venous thrombosis in surgical patients," Annals of Surgery 179, 278-290 each of which is hereby incorporated by reference in its entirety).

Disclosed is an inverse method which can extend hyperspectral imaging to detect parameters above and beyond oximetry that are specific to ulceration. For example, epidermal thickness can be a proxy for callus formation. Detection of water concentration can be used to detect inflammation, edema, and necrosis which affect the amount of water in the interstitial space. The predictive algorithm presented in JBO-001 is deficient in two ways. First, it is based entirely on OXY and DEOXY values and not on the rich set of biometric parameters enabled by wMC. Second, it provides a Boolean predictor for either ulceration or non-ulceration but does not provide a severity of probability of ulceration. The first deficiency is addressed in accordance with the present disclosure by repeating the clinical study reported in DC-001 and JBO-001 with wMC. This data can then be used to build a conditional predictor:

$$P(\text{ulceration}|\vec{b},\vec{p}) \qquad \text{Equation 18}$$

where the P is a conditional probability function, $\vec{b}$ is a vector of biometric parameters determined by the new HyperMed camera and wMC and $\vec{p}$ is patient data such as age, gender, and imaging location. The conditional probability function can be created using an approach such as Kernel Density Estimators (wikipedia.org/wiki/Kernel_density_estimation). This approach can be used to create "danger" maps where each pixel is assigned a probability of ulceration. Furthermore, the probability is specific to the patient age, gender, etc. This will be a patient specific ulcer prediction score and will thus exhibit a lower false positive rate.

Hyperspectral Imaging

Hyperspectral and multispectral imaging are related techniques in larger class of spectroscopy commonly referred to as spectral imaging or spectral analysis. Typically, hyperspectral imaging relates to the acquisition of a plurality of images, each image representing a narrow spectral band collected over a continuous spectral range, for example, 5 or more (e.g., 5, 10, 15, 20, 25, 30, 40, 50, or more) spectral bands having a FWHM bandwidth of 1 nm or more each (e.g., 1 nm, 2 nm, 3 nm, 4 nm, 5 nm, 10 nm, 20 nm or more), covering a contiguous spectral range (e.g., from 400 nm to 800 nm). In contrast, multispectral imaging relates to the acquisition of a plurality of images, each image representing a narrow spectral band collected over a discontinuous spectral range.

For the purposes of the present disclosure, the terms "hyperspectral" and "multispectral" are used interchangeably and refer to a plurality of images, each image representing a narrow spectral band (having a FWHM bandwidth of between 10 nm and 30 nm, between 5 nm and 15 nm, between 5 nm and 50 nm, less than 100 nm, between 1 and 100 nm, etc.), whether collected over a continuous or discontinuous spectral range. For example, in some implementations, wavelengths 1–N of a hyperspectral data cube 1336-1 are contiguous wavelengths or spectral bands covering a contiguous spectral range (e.g., from 400 nm to 800 nm). In other implementations, wavelengths 1–N of a hyperspectral data cube 1336-1 are non-contiguous wavelengths or spectral bands covering a non-contiguous spectral ranges (e.g., from 400 nm to 440 nm, from 500 nm to 540 nm, from 600 nm to 680 nm, and from 900 to 950 nm).

As used herein, "narrow spectral range" refers to a continuous span of wavelengths, typically consisting of a FWHM spectral band of no more than about 100 nm. In certain embodiments, narrowband radiation consists of a FWHM spectral band of no more than about 75 nm, 50 nm, 40 nm, 30 nm, 25 nm, 20 nm, 15 nm, 10 nm, 5 nm, 4 nm, 3 nm, 2 nm, 1 nm, or less. In some implementations, wavelengths imaged by the methods and devices disclosed herein are selected from one or more of the visible, near-infrared, short-wavelength infrared, mid-wavelength infrared, long-wavelength infrared, and ultraviolet (UV) spectrums.

By "broadband" it is meant light that includes component wavelengths over a substantial portion of at least one band, e.g., over at least 20%, or at least 30%, or at least 40%, or at least 50%, or at least 60%, or at least 70%, or at least 80%, or at least 90%, or at least 95% of the band, or even the entire band, and optionally includes component wavelengths within one or more other bands. A "white light source" is considered to be broadband, because it extends over a substantial portion of at least the visible band. In certain embodiments, broadband light includes component wavelengths across at least 100 nm of the electromagnetic spectrum. In other embodiments, broadband light includes component wavelengths across at least 150 nm, 200 nm, 250 nm, 300 nm, 400 nm, 500 nm, 600 nm, 700 nm, 800 nm, or more of the electromagnetic spectrum.

By "narrowband" it is meant light that includes components over only a narrow spectral region, e.g., less than 20%, or less than 15%, or less than 10%, or less than 5%, or less than 2%, or less than 1%, or less than 0.5% of a single band. Narrowband light sources need not be confined to a single band, but can include wavelengths in multiple bands. A plurality of narrowband light sources may each individually generate light within only a small portion of a single band, but together may generate light that covers a substantial portion of one or more bands, e.g., may together constitute a broadband light source. In certain embodiments, broadband light includes component wavelengths across no more than 100 nm of the electromagnetic spectrum (e.g., has a spectral bandwidth of no more than 100 nm). In other embodiments, narrowband light has a spectral bandwidth of no more than 90 nm, 80 nm, 75 nm, 70 nm, 60 nm, 50 nm, 40 nm, 30 nm, 25 nm, 20 nm, 15 nm, 10 nm, 5 nm, or less of the electromagnetic spectrum.

As used herein, the "spectral bandwidth" of a light source refers to the span of component wavelengths having an intensity that is at least half of the maximum intensity, otherwise known as "full width at half maximum" (FWHM) spectral bandwidth. Many light emitting diodes (LEDs) emit radiation at more than a single discreet wavelength, and are thus narrowband emitters. Accordingly, a narrowband light source can be described as having a "characteristic wavelength" or "center wavelength," i.e., the wavelength emitted with the greatest intensity, as well as a characteristic spectral bandwidth, e.g., the span of wavelengths emitted with an intensity of at least half that of the characteristic wavelength.

By "coherent light source" it is meant a light source that emits electromagnetic radiation of a single wavelength in phase. Thus, a coherent light source is a type of narrowband light source with a spectral bandwidth of less than 1 nm. Non-limiting examples of coherent light sources include lasers and laser-type LEDs. Similarly, an incoherent light source emits electromagnetic radiation having a spectral bandwidth of more than 1 nm and/or is not in phase. In this regard, incoherent light can be either narrowband or broadband light, depending on the spectral bandwidth of the light.

Examples of suitable broadband light sources 104 include, without limitation, incandescent lights such as a halogen lamp, xenon lamp, a hydrargyrum medium-arc iodide lamp, and a broadband light emitting diode (LED). In some embodiments, a standard or custom filter is used to balance the light intensities at different wavelengths to raise the signal level of certain wavelength or to select for a narrowband of wavelengths. Broadband illumination of a subject is particularly useful when capturing a color image of the subject or when focusing the hyperspectral/multispectral imaging system.

Examples of suitable narrowband, incoherent light sources 104 include, without limitation, a narrow band light emitting diode (LED), a superluminescent diode (SLD) (see, Redding B., arVix: 1110.6860 (2011), the content of which is hereby incorporated herein by reference in its entirety for all purposes), a random laser, and a broadband light source covered by a narrow band-pass filter. Examples of suitable narrowband, coherent light sources 104 include, without limitation, lasers and laser-type light emitting diodes. While both coherent and incoherent narrowband light sources 104 can be used in the imaging systems described herein, coherent illumination is less well suited for full-field imaging due to speckle artifacts that corrupt image formation (see, Oliver, B. M., *Proc IEEE* 51, 220-221 (1963)).

The conventional HSI system involves two scanning methods: spatial scanning and spectral scanning Spatial scanning methods generate hyperspectral images by acquiring a complete spectrum for each pixel in the case of whiskbroom (point-scanning) instruments or line of pixels in pushbroom (line-scanning) instruments, and then spatially scanning through the scene. Spectral scanning methods, also called staring or area-scanning imaging, involves capturing the whole scene with 2-D detector arrays in a single exposure and then stepping through wavelengths to complete the data cube.

Hyperspectral Medical Imaging

The disclosure provides systems and methods useful for hyperspectral/multispectral medical imaging (HSMI). HSMI relies upon distinguishing the interactions that occur between light at different wavelengths and components of the human body, especially components located in or just under the skin. For example, it is well known that deoxyhemoglobin absorbs a greater amount of light at 700 nm than does water, while water absorbs a much greater amount of light at 1200 nm, as compared to deoxyhemoglobin. By measuring the absorbance of a two-component system consisting of deoxyhemoglobin and water at 700 nm and 1200 nm, the individual contribution of deoxyhemoglobin and water to the absorption of the system, and thus the concentrations of both components, can readily be determined. By extension, the individual components of more complex systems (e.g., human skin) can be determined by measuring the absorption of a plurality of wavelengths of light reflected or backscattered off of the system.

The particular interactions between the various wavelengths of light measured by hyperspectral/multispectral imaging and each individual component of the system (e.g., skin) produces hyperspectral/multispectral signature, when the data is constructed into a hyperspectral/multispectral data cube. Specifically, different regions (e.g., different ROI on a single subject or different ROI from different subjects) interact differently with light depending on the presence of, e.g., a medical condition in the region, the physiological structure of the region, and/or the presence of a chemical in the region. For example, fat, skin, blood, and flesh all interact with various wavelengths of light differently from one another. A given type of cancerous lesion interacts with various wavelengths of light differently from normal skin, from non-cancerous lesions, and from other types of cancerous lesions. Likewise, a given chemical that is present (e.g., in the blood, or on the skin) interacts with various wavelengths of light differently from other types of chemicals. Thus, the light obtained from each illuminated region of a subject has a spectral signature based on the characteristics of the region, which signature contains medical information about that region.

The structure of skin, while complex, can be approximated as two separate and structurally different layers, namely the epidermis and dermis. These two layers have very different scattering and absorption properties due to differences of composition. The epidermis is the outer layer of skin. It has specialized cells called melanocytes that produce melanin pigments. Light is primarily absorbed in the epidermis, while scattering in the epidermis is considered negligible. For further details, see G. H. Findlay, "Blue Skin," British Journal of Dermatology 83(1), 127-134 (1970), the content of which is incorporated herein by reference in its entirety for all purposes.

The dermis has a dense collection of collagen fibers and blood vessels, and its optical properties are very different from that of the epidermis. Absorption of light of a bloodless dermis is negligible. However, blood-born pigments like oxy- and deoxy-hemoglobin and water are major absorbers of light in the dermis. Scattering by the collagen fibers and absorption due to chromophores in the dermis determine the depth of penetration of light through skin.

Light used to illuminate the surface of a subject will penetrate into the skin. The extent to which the light penetrates will depend upon the wavelength of the particular radiation. For example, with respect to visible light, the longer the wavelength, the farther the light will penetrate into the skin. For example, only about 32% of 400 nm violet light penetrates into the dermis of human skin, while greater than 85% of 700 nm red light penetrates into the dermis or beyond (see, Capinera J. L., Encyclopedia of Entomology, 2nd Edition, Springer Science (2008) at page 2854, the content of which is hereby incorporated herein by reference in its entirety for all purposes). For purposes of the present disclosure, when referring to "illuminating a tissue," "reflecting light off of the surface," and the like, it is meant that radiation of a suitable wavelength for detection is backscattered from a tissue of a subject, regardless of the distance into the subject the light travels. For example, certain wavelengths of infra-red radiation penetrate below the surface of the skin, thus illuminating the tissue below the surface of the subject.

Briefly, light from the illuminator(s) on the systems described herein penetrates the subject's superficial tissue and photons scatter in the tissue, bouncing inside the tissue many times. Some photons are absorbed by oxygenated hemoglobin molecules at a known profile across the spectrum of light. Likewise for photons absorbed by de-oxygenated hemoglobin molecules. The images resolved by the optical detectors consist of the photons of light that scatter back through the skin to the lens subsystem. In this fashion, the images represent the light that is not absorbed by the various chromophores in the tissue or lost to scattering within the tissue. In some embodiments, light from the illuminators that does not penetrate the surface of the tissue is eliminated by use of polarizers. Likewise, some photons bounce off the surface of the skin into air, like sunlight reflecting off a lake.

Accordingly, different wavelengths of light may be used to examine different depths of a subject's skin tissue. Generally, high frequency, short-wavelength visible light is useful for investigating elements present in the epidermis, while lower frequency, long-wavelength visible light is useful for investigating both the epidermis and dermis. Furthermore, certain infra-red wavelengths are useful for investigating the epidermis, dermis, and subcutaneous tissues.

In the visible and near-infrared (VNIR) spectral range and at low intensity irradiance, and when thermal effects are negligible, major light-tissue interactions include reflection, refraction, scattering and absorption. For normal collimated incident radiation, the regular reflection of the skin at the air-tissue interface is typically only around 4%-7% in the 250-3000 nanometer (nm) wavelength range. For further details, see R. R. Anderson and J. A. Parrish, "The optics of human skin," Journal of Investigative Dermatology 77(1), 13-19 (1981), the content of which is hereby incorporated by reference in its entirety for all purposes. When neglecting the air-tissue interface reflection and assuming total diffusion of incident light after the stratum corneum layer, the steady state VNIR skin reflectance can be modeled as the light that first survives the absorption of the epidermis, then reflects back toward the epidermis layer due the isotropic scattering in the dermis layer, and then finally emerges out of the skin after going through the epidermis layer again.

Accordingly, the systems and methods described herein can be used to diagnose and characterize a wide variety of medical conditions. In one embodiment, the concentration of one or more skin or blood component is determined in order to evaluate a medical condition in a patient. Non-limiting examples of components useful for medical evaluation include: deoxyhemoglobin levels, oxyhemoglobin levels, total hemoglobin levels, oxygen saturation, oxygen perfusion, hydration levels, total hematocrit levels, melanin levels, collagen levels, and bilirubin levels. Likewise, the pattern, gradient, or change over time of a skin or blood component can be used to provide information on the medical condition of the patient.

Non-limiting examples of conditions that can be evaluated by hyperspectral/multispectral imaging include: tissue ischemia, ulcer formation, ulcer progression, pressure ulcer formation, pressure ulcer progression, diabetic foot ulcer formation, diabetic foot ulcer progression, venous stasis, venous ulcer disease, peripheral artery disease, atherosclerosis, infection, shock, cardiac decompensation, respiratory insufficiency, hypovolemia, the progression of diabetes, congestive heart failure, sepsis, dehydration, hemorrhage, hemorrhagic shock, hypertension, cancer (e.g., detection, diagnosis, or typing of tumors or skin lesions), retinal abnormalities (e.g., diabetic retinopathy, macular degeneration, or corneal dystrophy), skin wounds, burn wounds, exposure to a chemical or biological agent, and an inflammatory response.

In one embodiment, the systems and methods described herein are used to evaluate tissue oximetery and correspondingly, medical conditions relating to patient health derived from oxygen measurements in the superficial vasculature. In certain embodiments, the systems and methods described herein allow for the measurement of oxygenated hemoglobin, deoxygenated hemoglobin, oxygen saturation, and oxygen perfusion. Processing of these data provide information to assist a physician with, for example, diagnosis, prognosis, assignment of treatment, assignment of surgery, and the execution of surgery for conditions such as critical limb ischemia, diabetic foot ulcers, pressure ulcers, peripheral vascular disease, surgical tissue health, etc.

In one embodiment, the systems and methods described herein are used to evaluate diabetic and pressure ulcers. Development of a diabetic foot ulcer is commonly a result of a break in the barrier between the dermis of the skin and the subcutaneous fat that cushions the foot during ambulation. This rupture can lead to increased pressure on the dermis, resulting in tissue ischemia and eventual death, and ultimately manifesting in the form of an ulcer (Frykberg R. G. et al., Diabetes Care 1998; 21(10):1714-9). Measurement of oxyhemoglobin, deoxyhemoglobin, and/or oxygen saturation levels by hyperspectral/multispectral imaging can provide medical information regarding, for example: a likelihood of ulcer formation at an ROI, diagnosis of an ulcer, identification of boundaries for an ulcer, progression or regression of ulcer formation, a prognosis for healing of an ulcer, the likelihood of amputation resulting from an ulcer. Further information on hyperspectral/multispectral methods for the detection and characterization of ulcers, e.g., diabetic foot ulcers, are found in U.S. Patent Application Publication No. 2007/0038042, and Nouvong A. et al., Diabetes Care. 2009 November; 32(11):2056-61, the contents of which are hereby incorporated herein by reference in their entireties for all purposes.

Other examples of medical conditions include, but are not limited to: tissue viability (e.g., whether tissue is dead or living, and/or whether it is predicted to remain living); tissue ischemia; malignant cells or tissues (e.g., delineating malignant from benign tumors, dysplasias, precancerous tissue, metastasis); tissue infection and/or inflammation; and/or the presence of pathogens (e.g., bacterial or viral counts). Some embodiments include differentiating different types of tissue from each other, for example, differentiating bone from flesh, skin, and/or vasculature. Some embodiments exclude the characterization of vasculature.

In yet other embodiments, the systems and methods provided herein can be used during surgery, for example to determine surgical margins, evaluate the appropriateness of surgical margins before or after a resection, evaluate or monitor tissue viability in near-real time or real-time, or to assist in image-guided surgery. For more information on the use of hyperspectral/multispectral imaging during surgery, see, Holzer M. S. et al., J Urol. 2011 August; 186(2):400-4; Gibbs-Strauss S. L. et al., Mol Imaging. 2011 April; 10(2): 91-101; and Panasyuk S. V. et al., Cancer Biol Ther. 2007 March; 6(3):439-46, the contents of which are hereby incorporated herein by reference in their entirety for all purposes.

For more information on the use of hyperspectral/multispectral imaging in medical assessments, see, for example: Chin J. A. et al., J Vasc Surg. 2011 December; 54(6):1679-88; Khaodhiar L. et al., Diabetes Care 2007; 30:903-910; Zuzak K. J. et al., Anal Chem. 2002 May 1; 74(9):2021-8; Uhr J. W. et al., Transl Res. 2012 May; 159(5):366-75; Chin M. S. et al., J Biomed Opt. 2012 February; 17(2):026010; Liu Z. et al., Sensors (Basel). 2012; 12(1):162-74; Zuzak K. J. et al., Anal Chem. 2011 Oct. 1; 83(19):7424-30; Palmer G. M. et al., J Biomed Opt. 2010 November-December; 15(6): 066021; Jafari-Saraf and Gordon, Ann Vasc Surg. 2010 August; 24(6):741-6; Akbari H. et al., IEEE Trans Biomed Eng. 2010 August; 57(8):2011-7; Akbari H. et al., Conf Proc IEEE Eng Med Biol Soc. 2009:1461-4; Akbari H. et al., Conf Proc IEEE Eng Med Biol Soc. 2008:1238-41; Chang S. K. et al., Clin Cancer Res. 2008 Jul. 1; 14(13):4146-53; Siddiqi A. M. et al., Cancer. 2008 Feb. 25; 114(1):13-21; Liu Z. et al., Appl Opt. 2007 Dec. 1; 46(34):8328-34; Zhi L. et al., Comput Med Imaging Graph. 2007 December; 31(8): 672-8; Khaodhiar L. et al., Diabetes Care. 2007 April; 30(4):903-10; Ferris D. G. et al., J Low Genit Tract Dis. 2001 April; 5(2):65-72; Greenman R. L. et al., Lancet. 2005 Nov. 12; 366(9498):1711-7; Sorg B. S. et al., J Biomed Opt. 2005 July-August; 10(4):44004; Gillies R. et al., and Diabetes Technol Ther. 2003; 5(5):847-55, the contents of which are hereby incorporated herein by reference in their entirety for all purposes.

In yet other embodiments, the systems and methods provided herein can be used during surgery, for example to determine surgical margins, evaluate the appropriateness of surgical margins before or after a resection, evaluate or monitor tissue viability in near-real time or real-time, or to assist in image-guided surgery. For more information on the use of hyperspectral/multispectral imaging during surgery, see, Holzer M. S. et al., J Urol. 2011 August; 186(2):400-4; Gibbs-Strauss S. L. et al., Mol Imaging. 2011 April; 10(2): 91-101; and Panasyuk S. V. et al., Cancer Biol Ther. 2007 March; 6(3):439-46, the contents of which are hereby incorporated herein by reference in their entirety for all purposes.

It will also be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A computer implemented method, performed by a computer system having one or more processors and memory storing one or more programs for execution by the one or more processors, the method comprising:

acquiring a hyperspectral imaging data set from a region of interest of a human subject using a hyperspectral imager; and applying the hyperspectral imaging data set against a classifier comprising a two layered media model, the two layered media model comprising a first layer of a modeled human tissue overlying a second layer of the modeled human tissue, wherein the two layered media model has been trained by application of simulated data across a set of optical and geometric properties associated with the presence or the absence of a skin indication, wherein the two layered media model computes tissue reflectance R from the modeled human tissue by the relationship:

$$R = \sum_{i=0}^{\infty} \sum_{j=0}^{\infty} \exp(i\tilde{\omega}_1 + j\tilde{\omega}_2) P(i, j \mid L_1)$$

wherein,
$L_1$ is the thickness of the first layer,
$\tilde{\omega}_1$ is a modified single scattering of the first layer,
$\tilde{\omega}_2$ is a modified single scattering of the second layer,
exp is the exponential function, and
$P(i,j|L_1)$ is a joint probability density function that a photon will experience i interactions with the first layer and j interactions with the second layer given that the first layer thickness is $L_1$, wherein the application of the hyperspectral imaging data set against the classifier causes the classifier to produce a determination as to whether the region of interest has the skin indication.

2. The computer implemented method of claim 1, wherein the determination as to whether the region of interest has the skin indication is a likelihood that the region of interest has the skin indication.

3. The computer implemented method of claim 1, wherein the determination as to whether the region of interest has the skin indication is either a determination that the region of interest has the skin indication or a determination that the region of interest does not have the skin indication.

4. The computer implemented method of claim 1, the method further comprising training the model using the trajectory vector $\vec{x}_p$ of each respective photon p in a set of photons comprising a million or more photons.

5. The computer implemented method of claim 4, wherein, for each respective photon in the set of photons, the trajectory vector $\vec{x}_p$ of the respective photon was calculated such that $\vec{x}_{p,k} = \langle x, y, z \rangle_k$ represents the location of the $k^{th}$ interaction between the photon and the two layer model and wherein the trajectory vector $\vec{x}_p$ was stored in a non-transitory data file.

6. The computer implemented method of claim 5, wherein $P(i,j|L_1)$ is approximated as $$\frac{N(i, j \mid L_1)}{P}$$

wherein $N(i,j|L_1)$ is a count of the set of photons in the set of photons that experience i interactions with the first layer and j interactions with the second layer given $L_1$, and has the form:

$$N(i, j \mid L_1) = \sum_{p=1}^{p=P} \begin{cases} 1 & N_{p,1} = i \text{ and } N_{p,2} = j \\ 0 & \text{otherwise} \end{cases}$$

wherein,
$N_{p,1}$ is a number of interactions between photon p and the first layer,
$N_{p,2}$ is a number of interactions between photon p and the second layer, and
P is the number of photons in the set of photons.

7. The computer implemented method of claim 4, wherein the trajectory vector $\vec{x}_p$ of each respective photon p in the set of photons is computed using a scaled or white Monte Carlo simulation.

8. The computer implemented method of claim 1, wherein the hyperspectral imaging data set comprises a plurality of images of the region of interest, each respective image in the plurality of images acquired at a wavelength in one or more of the ultra-violet (UV), visible, near infra-red (NIR), and infra-red (IR) spectral regions.

9. The computer implemented method of claim 8, wherein at least one respective image in the plurality of images is acquired at a wavelength in the visible spectral region and at least one respective image in the plurality of images is acquired at a wavelength in the NIR spectral region.

10. The computer implemented method of claim 1, wherein the hyperspectral imaging data set comprises a plurality of images of the region of interest, each respective image in the plurality of images acquired at a wavelength in the visible or NIR spectral regions.

11. The computer implemented method according to claim 1, wherein the hyperspectral imaging data set comprises a plurality of images acquired without contacting the human subject.

12. The computer implemented method according to claim 1, wherein the hyperspectral imaging data set comprises a plurality of images acquired endoscopically, laparoscopically, thoracoscopically, cystoscopically, hysteroscopically, bronchoscopically, or mediastinoscopically.

13. The computer implemented method according to claim 1, wherein the hyperspectral imaging data set comprises a plurality of images of the region of interest, the method further comprising:
prior to applying the hyperspectral imaging data set against the classifier, pre-processing at least one image in the plurality of images by performing at least one of:
i.) adjusting the brightness of the image,
ii.) adjusting the contrast of the image,
iii.) removing an artifact from the image,
iv.) cropping the image,
v.) processing one or more sub-pixels of the image,
vi.) compressing the size of the image,
vii.) assembling a plurality of images into a spectral hypercube,
viii.) transforming a spectral hypercube assembled from the plurality of images,
ix.) formatting data contained within the image, and
x.) encrypting data contained within the image.

14. The computer implemented method according to claim 1, wherein the hyperspectral imaging data set is transmitted to a remote computer system by wireless communication.

15. The computer implemented method of claim 14, wherein the remote computer system is a mobile device, and the transmission is by wired or wireless communication.

16. The computer implemented method according claim 15, wherein the mobile device is selected from the group consisting of a smart phone, a personal digital assistant (PDA), an enterprise digital assistant, a tablet computer, a digital camera, and a portable music player.

17. The computer implemented method according to claim 1, wherein the skin indication is selected from the group consisting of tissue ischemia, an ulcer, peripheral artery disease, atherosclerosis, chronic venous insufficiency, lower extremity deep venous thrombosis, infection, shock, hypovolemia, diabetes, dehydration, hemorrhage, hemorrhagic shock, hypertension, cancer, a retinal abnormality, a skin wound, a burn wound, exposure to a chemical or biological agent, and an inflammatory response.

18. The computer implemented method according to claim 1, wherein the skin indication is a diabetic foot ulcer.

19. The computer implemented method of claim 1 wherein the set of optical and geometric properties comprises tissue oxygen saturation $SO_2$, total hemoglobin concentration $f_{HEME}$, melanin concentration $f_{mel}$, tissue water concentration $f_{H_2O}$, epidermal thickness $L_1$ and wavelength range.

20. The computer implemented method of claim 19, wherein the training was performed with $SO_2$ between 0% and 100%, $f_{HEME}$ between 0 and 200 µM, $f_{mel}$ between 0.002 µM and 0.15 µM, $f_{H_2O}$ between 0 and 100%, and $L_1$ between 10 µm and 150 µm.

21. The computer implemented method of claim 19, wherein the training was performed at each of between 5 and 20 wavelengths.

22. The computer implemented method of claim 1, wherein the skin indication is an ulcer, the method further comprising:
  detecting at least one physiological change selected from:
  (i) inflammation of the ulcer and surrounding areas,
  (ii) necrosis,
  (iii) callus formation around the ulcer site,
  (iv) loss of the epidermal layer, and
  (v) hyper-pigmentation.

23. The computer implemented method of claim 1, wherein the classifier is an interpolation table that stores R as a function of the set of optical and geometric properties associated with the presence or the absence of a skin indication.

24. The computer implemented method of claim 1, wherein the classifier is an artificial neural network that stores a relationship between an input parameter and output parameters, wherein the artificial neural network is trained by computed reflectance R calculated by the two layered media model as an input parameter and the set of optical and geometric properties as output parameters.

25. The computer implemented method of claim 1, wherein the first layer is a melanin pigmented epidermis and the second layer is a blood pigmented dermis.

26. A computer system, comprising
  one or more processors;
  memory; and
  one or more programs, the one or more programs stored in the memory and configured to be executed by the one or more processors, the one or more programs including instructions for:
    acquiring a hyperspectral imaging data set from a region of interest of a human subject collected by a hyperspectral imager; and
    applying the hyperspectral imaging data set against a classifier comprising a two layered media model, the two layered media model comprising a first layer of a modeled human tissue overlying a second layer of the modeled human tissue, wherein the two layered media model has been trained by application of simulated data across a set of optical and geometric properties associated with the presence or the absence of a skin indication, wherein the two layered media model computes tissue reflectance R from the modeled human tissue by the relationship:

$$R = \sum_{i=0}^{\infty} \sum_{j=0}^{\infty} \exp(i\tilde{\omega}_1 + j\tilde{\omega}_2) P(i, j \mid L_1)$$

wherein,
  $L_1$ is the thickness of the first layer,
  $\tilde{\omega}_1$ is a modified single scattering of the first layer,
  $\tilde{\omega}_2$ is a modified single scattering of the second layer,
  exp is the exponential function, and
  $P(i,j|L_1)$ is a joint probability density function that a photon will experience i interactions with the first layer and j interactions with the second layer given that the first layer thickness is $L_1$,
wherein the application of the hyperspectral imaging data set against the classifier causes the classifier to produce a determination as to whether the region of interest has the skin indication.

27. A computer implemented method, performed by a computer system having one or more processors and memory storing one or more programs for execution by the one or more processors, the method comprising:
  acquiring a hyperspectral imaging data set from a region of interest of a human subject using a hyperspectral imager; and
  applying the hyperspectral imaging data set against a classifier comprising a two layered media model, the two layered media model comprising a first layer of a modeled human tissue overlying a second layer of the modeled human tissue, wherein the two layered media model has been trained by application of simulated data from a set of photons across a set of optical and geometric properties associated with the presence or the absence of a skin indication, wherein the two layered media model computes tissue reflectance R from the modeled human tissue by the relationship:

$$R = \frac{W_{total}}{P} = W_0 \sum_{i=0}^{\infty} \sum_{j=0}^{\infty} (\omega_1)^i (\omega_2)^j P(i, j \mid L_1)$$

wherein,
  $W_{total}$ is the total energy remitted by the set of photons,
  P is the number of photons in the set of photons,
  $W_0$ is the initial energy of each photon in the set of photons,
  $\omega_1$ is the single scattering albedo of the first layer,
  $\omega_2$ is the single scattering albedo of the second layer,
  $L_1$ is the thickness of the first layer,
  $P(i,j|L_1)$ is a joint probability density function that a respective photon in the set of photons will experience i interactions with the first layer and j interactions with the second layer given the first layer thickness $L_1$,
  wherein the application of the hyperspectral imaging data set against the classifier causes the classifier to produce a determination as to whether the region of interest has the skin indication.

28. The computer implemented method of claim 27, wherein the two layer model requires $$\mu_{a,1} + \mu_{s,1} = \mu_{a,2} + \mu_{s,2} = 1 \text{ cm}^{-1},$$

wherein,
  $\mu_{a,1}$ is the absorption interaction coefficient for the first layer,
  $\mu_{s,1}$ is the scattering interaction coefficient for the first layer, $\mu_{a,2}$ is the absorption interaction coefficient for the second layer, and
$\mu_{s,2}$ is the scattering interaction coefficient for the second layer.

29. The computer implemented method of claim 27, wherein the determination as to whether the region of interest has the skin indication is a likelihood that the region of interest has the skin indication.

30. The computer implemented method of claim 27, wherein $P(i,j|L_1)$ is approximated as $$\frac{N(i,j|L_1)}{P}$$

wherein $N(i,j|L_1)$ is a count of the number of photons in the set of photons that experience i interactions with the first layer and j interactions with the second layer given $L_1$, and has the form:

$$N(i,j|L_1) = \sum_{p=1}^{p=P} \begin{cases} 1 & N_{p,1}=i \text{ and } N_{p,2}=j \\ 0 & \text{otherwise} \end{cases}$$

wherein,
$N_{p,1}$ is a number of interactions between respective photon p and the first layer,
$N_{p,2}$ is a number of interactions between respective photon p and the second layer, and
P is the number of photons in the set of photons.

31. The computer implemented method of claim 27, wherein the two layer model allows $\mu_{a,1} + \mu_{s,1} \neq 1$, wherein,
$\mu_{a,1}$ is the absorption interaction coefficient for the first layer, and
$\mu_{s,1}$ is the scattering interaction coefficient for the first layer.

32. The computer implemented method of claim 31, wherein $P(i,j|L_1) = P(i,j|\tilde{L}_1) = P(i,j|\tilde{L}_1, \tilde{\mu}_{a,1}, \tilde{\mu}_{s,1})$ wherein, $$\frac{\mu_{a,1}}{\mu_{t,1}} \to \tilde{\mu}_{a,1},$$

$$\frac{\mu_{s,1}}{\mu_{t,1}} \to \tilde{\mu}_{s,1},$$

$$\mu_{t,1} = \mu_{a,1} + \mu_{s,1},$$

$$L_1 \mu_{t,1} \to \tilde{L}_1, \text{ and}$$

" $\to$ " indicates equivalence under $P(i,j|L_1)$.

33. The computer implemented method of claim 27, wherein the two layer model allows $\mu_{a,2} + \mu_{s,2} \neq 1$, wherein,
$\mu_{a,2}$ is the absorption interaction coefficient for the second layer, and
$\mu_{s,2}$ is the scattering interaction coefficient for the second layer.

34. The computer implemented method of claim 33, wherein $P(i,j|L_1) = P(i,j|\tilde{L}_1) = P(i,j|\tilde{L}_1, \tilde{\mu}_{a,1}, \tilde{\mu}_{t,2}=1, \omega_2)$ wherein,
$\mu_{a,1}$ is the absorption interaction coefficient for the first layer, and
$\mu_{s,1}$ is the scattering interaction coefficient for the first layer, $$\mu_{t,1} = \mu_{a,1} + \mu_{s,1},$$

$$\frac{\mu_{a,1}}{\mu_{t,1}} \to \tilde{\mu}_{a,1},$$

$$\frac{\mu_{s,1}}{\mu_{t,1}} \to \tilde{\mu}_{s,1},$$

$$L_1 \mu_{t,1} \to \tilde{L}_1, \text{ and}$$

" $\to$ " indicates equivalence under $P(i,j|L_1)$.

35. A computer system, comprising
one or more processors;
memory; and
one or more programs, the one or more programs stored in the memory and configured to be executed by the one or more processors, the one or more programs including instructions for:
acquiring a hyperspectral imaging data set from a region of interest of a human subject collected by a hyperspectral imager; and
applying the hyperspectral imaging data set against a classifier comprising a two layered media model, the two layered media model comprising a first layer of a modeled human tissue overlying a second layer of the modeled human tissue, wherein the two layered media model has been trained by application of simulated data from a set of photons across a set of optical and geometric properties associated with the presence or the absence of a skin indication, wherein the two layered media model computes tissue reflectance R from the modeled human tissue by the relationship:

$$R = \frac{W_{total}}{P} = W_0 \sum_{i=0}^{\infty} \sum_{j=0}^{\infty} (\omega_1)^i (\omega_2)^j P(i,j|L_1)$$

wherein,
$W_{total}$ is the total energy remitted by the set of photons,
P is the number of photons in the set of photons,
$W_0$ is the initial energy of each photon in the set of photons,
$\omega_1$ is the single scattering albedo of the first layer,
$\omega_2$ is the single scattering albedo of the second layer,
$L_1$ is the thickness of the first layer,
$P(i,j|L_1)$ is a joint probability density function that a respective photon in the set of photons will experience i interactions with the first layer and j interactions with the second layer given the first layer thickness $L_1$,
wherein the application of the hyperspectral imaging data set against the classifier causes the classifier to produce a determination as to whether the region of interest has the skin indication.

36. A computer implemented method, performed by a computer system having one or more processors and memory storing one or more programs for execution by the one or more processors, the method comprising:

acquiring a hyperspectral imaging data set from a region of interest of a human subject using a hyperspectral imager; and applying the hyperspectral imaging data set against a classifier comprising a two layered media model, the two layered media model comprising a first layer of a modeled human tissue overlying a second layer of the modeled human tissue, wherein the two layered media model has been trained by application of simulated data from a set of photons across a set of optical and geometric properties associated with the presence or the absence of a skin indication, wherein the two layered media model computes tissue reflectance R from the modeled human tissue by the relationship:

$$R = \alpha_0 \sum_{i=0}^{\infty} \sum_{j=0}^{\infty} \exp(i\tilde{\omega}_1 + j\tilde{\omega}_2) P(i, j \mid \tilde{L}_1)$$

wherein, $\alpha_0$ is a constant for losses arising from surface reflectance or the acceptance angle of the hyperspectral imager, exp is the exponential function, i is an integer, j is an integer, $\tilde{\omega}_1 = \log \omega_1$, $\tilde{\omega}_2 = \log \omega_2$, $\omega_1$ is the single scattering albedo of the first layer, $\omega_2$ is the single scattering albedo of the second layer, $\tilde{L}_1 = L_1 \mu_{t,1}$, $\mu_{t,1}$ is the total interaction coefficient of the first layer, $L_1$ is the thickness of the top layer, and $P(i,j|L_1)$ is a joint probability density function that a photon in the set of photons will experience i interactions with the first layer and j interactions with the second layer given $\tilde{L}_1$.

37. A computer system, comprising one or more processors;

memory; and one or more programs, the one or more programs stored in the memory and configured to be executed by the one or more processors, the one or more programs including instructions for:

acquiring a hyperspectral imaging data set from a region of interest of a human subject collected by a hyperspectral imager; and applying the hyperspectral imaging data set against a classifier comprising a two layered media model, the two layered media model comprising a first layer of a modeled human tissue overlying a second layer of the modeled human tissue, wherein the two layered media model has been trained by application of simulated data from a set of photons across a set of optical and geometric properties associated with the presence or the absence of a skin indication, wherein the two layered media model computes tissue reflectance R from the modeled human tissue by the relationship:

$$R = \alpha_0 \sum_{i=0}^{\infty} \sum_{j=0}^{\infty} \exp(i\tilde{\omega}_1 + j\tilde{\omega}_2) P(i, j \mid \tilde{L}_1)$$

wherein, $\alpha_0$ is a constant for losses arising from surface reflectance or the acceptance angle of the hyperspectral imager, exp is the exponential function, i is an integer, j is an integer, $\tilde{\omega}_1 = \log \omega_1$, $\tilde{\omega}_2 = \log \omega_2$, $\omega_1$ is the single scattering albedo of the first layer, $\omega_2$ is the single scattering albedo of the second layer, $\tilde{L}_1 = L_1 \mu_{t,1}$, $\mu_{t,1}$ is the total interaction coefficient of the first layer, $L_1$ is the thickness of the top layer, and $P(i,j|L_1)$ is a joint probability density function that a photon in the set of photons will experience i interactions with the first layer and j interactions with the second layer given $L_1$.

* * * * *